United States Patent
Shiraishi

(10) Patent No.: US 10,231,658 B2
(45) Date of Patent: Mar. 19, 2019

(54) ENDOSCOPE SYSTEM, PROCESSOR DEVICE FOR ENDOSCOPE SYSTEM, OPERATION METHOD FOR ENDOSCOPE SYSTEM, AND OPERATION METHOD FOR PROCESSOR DEVICE

(71) Applicant: FUJIFILM Corporation, Tokyo (JP)

(72) Inventor: Yasushi Shiraishi, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 461 days.

(21) Appl. No.: 15/058,391

(22) Filed: Mar. 2, 2016

(65) Prior Publication Data

US 2016/0174886 A1 Jun. 23, 2016

Related U.S. Application Data

(63) Continuation of application No. PCT/JP2014/068764, filed on Jul. 15, 2014.

(30) Foreign Application Priority Data

Sep. 26, 2013 (JP) .................................. 2013-200653
Nov. 13, 2013 (JP) .................................. 2013-235460

(51) Int. Cl.
*A61B 5/1455* (2006.01)
*A61B 1/00* (2006.01)
(Continued)

(52) U.S. Cl.
CPC ........ *A61B 5/14551* (2013.01); *A61B 1/0005* (2013.01); *A61B 1/00009* (2013.01);
(Continued)

(58) Field of Classification Search
CPC ... A61B 5/0059; A61B 5/0071; A61B 5/0084; A61B 5/14542; A61B 5/14503;
(Continued)

(56) References Cited

U.S. PATENT DOCUMENTS

4,998,973 A * 3/1991 Kikuchi .................. A61B 1/05
348/68
5,795,295 A * 8/1998 Hellmuth ............. A61B 5/0059
250/201.3

(Continued)

FOREIGN PATENT DOCUMENTS

JP 2010-167045 A 8/2010
JP 2012-125402 A 7/2012
(Continued)

OTHER PUBLICATIONS

Extended European Search Report, dated Dec. 19, 2016 for European Application No. 14848419.9.
(Continued)

*Primary Examiner* — Eric Winakur
*Assistant Examiner* — Chu Chuan (JJ) Liu
(74) *Attorney, Agent, or Firm* — Birch, Stewart, Kolasch & Birch, LLP

(57) ABSTRACT

Information for assisting a doctor based on the oxygen saturation of an observation target is presented. An endoscope system includes a light source device, an image sensor, an oxygen saturation calculation unit, a distribution pattern generation unit, a disease state score calculation unit, and a monitor. The light source device emits light to irradiate the observation target. The image sensor images the observation target with reflected light of the light, and outputs an image signal. The oxygen saturation calculation unit calculates an oxygen saturation of the observation target based on the image signal. The distribution pattern generation unit generates a distribution pattern showing the distribution of the oxygen saturation. The disease state score calculation unit calculates a disease state score indicating the disease state of the observation target based on the distribution
(Continued)

pattern. The monitor displays the disease state score or information based on the disease state score.

29 Claims, 25 Drawing Sheets

(51) Int. Cl.
    *A61B 1/04*         (2006.01)
    *A61B 1/06*         (2006.01)
    *A61B 5/1459*     (2006.01)
    *A61B 5/00*         (2006.01)
    *A61B 5/145*      (2006.01)
    *G16H 50/30*     (2018.01)
    *G06F 19/00*     (2018.01)

(52) U.S. Cl.
    CPC ............ *A61B 1/00045* (2013.01); *A61B 1/04* (2013.01); *A61B 1/043* (2013.01); *A61B 1/0646* (2013.01); *A61B 5/0071* (2013.01); *A61B 5/0084* (2013.01); *A61B 5/1459* (2013.01); *A61B 5/14503* (2013.01); *A61B 5/14542* (2013.01); *G06F 19/00* (2013.01); *G16H 50/30* (2018.01)

(58) Field of Classification Search
    CPC . A61B 5/1459; A61B 5/1455; A61B 5/14551; A61B 5/14552; A61B 5/72; A61B 1/0009; A61B 1/00045; A61B 1/04; A61B 1/043; A61B 1/0646
    See application file for complete search history.

(56) References Cited

U.S. PATENT DOCUMENTS

| | | | | |
|---|---|---|---|---|
| 2002/0019587 | A1* | 2/2002 | Cheng | A61B 5/14546 600/322 |
| 2011/0230715 | A1* | 9/2011 | Saito | A61B 1/00009 600/109 |
| 2012/0053434 | A1* | 3/2012 | Saito | A61B 1/00009 600/324 |
| 2012/0157803 | A1* | 6/2012 | Saito | A61B 1/00009 600/325 |
| 2012/0253157 | A1 | 10/2012 | Yamaguchi et al. | |
| 2012/0253158 | A1 | 10/2012 | Yamaguchi et al. | |
| 2013/0018242 | A1 | 1/2013 | Yamaguchi et al. | |

FOREIGN PATENT DOCUMENTS

| | | |
|---|---|---|
| JP | 2012-213550 A | 11/2012 |
| JP | 2012-213551 A | 11/2012 |

OTHER PUBLICATIONS

IPR, with English Translation, of the International Searching Authority, issued in PCT/JP2014/068754, dated Mar. 29, 2016.
International Search Report, issued in PCT/JP2014/068764, dated Oct. 7, 2014.
Written Opinion of the International Searching Authority, issued in PCT/JP2014/068764, dated Oct. 7, 2014.
Partial Supplementary European Search Report, dated Sep. 13, 2016, for corresponding European Application No. 14848419.9.
Japanese Notification of Reasons for Refusal for Japanese Application No. 2013-235460, dated Nov. 2, 2016, with a machine translation.

* cited by examiner

ENDOSCOPE SYSTEM, PROCESSOR DEVICE FOR ENDOSCOPE SYSTEM, OPERATION METHOD FOR ENDOSCOPE SYSTEM, AND OPERATION METHOD FOR PROCESSOR DEVICE

CROSS-REFERENCE TO RELATED APPLICATIONS

This application is a Continuation of PCT International Application No. PCT/JP2014/068764 filed on Jul. 15, 2014, which claims priority under 35 U.S.C § 119(a) to Japanese Patent Application No. 2013-200653 filed on Sep. 26, 2013 and Japanese Patent Application No. 2013-235460 filed on Nov. 13, 2013. Each of the above application(s) is hereby expressly incorporated by reference, in its entirety, into the present application.

BACKGROUND OF THE INVENTION

1. Field of the Invention

The present invention relates to an endoscope system, a processor device for an endoscope system, an operation method for an endoscope system, and an operation method for a processor device for calculating biological function information regarding the oxygen saturation of blood hemoglobin from an image signal obtained by imaging an observation target in a subject.

2. Description of the Related Art

In the medical field, it is common to perform diagnosis using an endoscope system including a light source device, an endoscope, and a processor device. In recent years, diagnosis of a lesion using the oxygen saturation of blood hemoglobin, among the pieces of biological function information, has been performed. In particular, it is possible to determine the normal tissue and the cancer tissue based on the oxygen saturation (JP2012-213550A and JP2012-125402A). In JP2012-213550A, the distributions of the oxygen saturation of the surface layer, the intermediate layer, and the deep layer of the observation target are displayed by changing the combination of emitted light, so that it is possible to determine the state of the cancer tissue in more detail.

As a method of acquiring the oxygen saturation, a method is known in which first signal light and second signal light having different wavelength bands and different absorption coefficients for oxygenated hemoglobin and reduced hemoglobin alternately irradiate blood vessels in the mucous membrane and the reflected light beams of the first and the second signal light beams are detected by a sensor located at the distal portion of the endoscope (refer to JP2012-213550A and JP2012-125402A).

A ratio between a first signal light image signal corresponding to the reflected light of the first signal light detected by the sensor and a second signal light image signal corresponding to the reflected light of the second signal light detected by the sensor (hereinafter, referred to as a signal ratio) is maintained at a fixed value in a case where there is no change in oxygen saturation in blood vessels. However, in a case where a change in oxygen saturation occurs, the signal ratio changes with the oxygen saturation change. Accordingly, it is possible to calculate the oxygen saturation based on the signal ratio between the first signal light image signal and the second signal light image signal.

SUMMARY OF THE INVENTION

In a case where "oxygen saturation" or an "image showing the oxygen saturation (hereinafter, referred to as an oxygen saturation image)" is presented, a doctor can determine the presence of the cancer tissue based on this. In particular, as in JP2012-213550A, In a case where the endoscope system presents the distribution of the oxygen saturation of the surface layer, the intermediate layer, and the deep layer of the observation target, a doctor can determine the cancer tissue more accurately.

However, since the accuracy of diagnosis based on such an oxygen saturation image largely depends on the knowledge or experience (skill) of a doctor, there may be a variation in the diagnostic result. For example, even if the cancer tissue can be found based on the oxygen saturation image, a detailed diagnostic result, such as the degree of progression (for example, stage classification), may change doctor to doctor. In addition, the degree of progression of cancer may not be able to be determined based on only various images provided by the endoscope system, such as an oxygen saturation image.

It is an object of the present invention to provide an endoscope system, a processor device for an endoscope system, an operation method for an endoscope system, and an operation method for a processor device to present information for assisting a doctor in performing more accurate and detailed diagnosis based on the oxygen saturation of the observation target.

An endoscope system of the present invention includes a light source device, an image sensor, an oxygen saturation calculation unit, a distribution pattern generation unit, a disease state score calculation unit, and a display unit. The light source device emits light to irradiate an observation target. The image sensor images the observation target with reflected light of the light emitted from the light source device, and outputs an image signal. The oxygen saturation calculation unit calculates an oxygen saturation of the observation target based on the image signal. The distribution pattern generation unit generates a distribution pattern showing a distribution of the oxygen saturation. The disease state score calculation unit calculates a disease state score indicating a disease state of the observation target based on the distribution pattern. The display unit displays the disease state score or information based on the disease state score.

It is preferable that the disease state score in a case in which a high oxygen region having the oxygen saturation equal to or greater than a predetermined value is present in a low oxygen region having the oxygen saturation less than the predetermined value is greater than the disease state score in a case in which the high oxygen region is not present in the low oxygen region. In addition, it is preferable that, in a case in which the high oxygen region is present in the low oxygen region, the disease state score increases as a proportion of the high oxygen region with respect to the low oxygen region increases.

In contrast, the disease state score in a case in which a high oxygen region having the oxygen saturation equal to or greater than a predetermined value is present in a low oxygen region having the oxygen saturation less than the predetermined value may be smaller than the disease state score in a case in which the high oxygen region is not present in the low oxygen region. In this case, in a case in which the high oxygen region is present in the low oxygen region, the disease state score decreases as a proportion of the high oxygen region with respect to the low oxygen region increases.

For example, the disease state score calculation unit compares the distribution pattern calculated by the distribution pattern generation unit with a reference pattern of a specific distribution shape, and calculates a similarity between the reference pattern and the distribution pattern calculated by the distribution pattern generation unit as the disease state score. The reference pattern of the specific distribution shape is a pattern in which a high oxygen region having the oxygen saturation equal to or greater than a predetermined value is present in a low oxygen region having the oxygen saturation less than the predetermined value.

The distribution pattern generation unit may generate the distribution pattern for a region of interest designated in advance. In this case, the disease state score calculation unit calculates the disease state score for the region of interest.

The endoscope system may further include a similar clinical data selection unit. The similar clinical data selection unit compares the distribution pattern with clinical data referring to a database in which a plurality of pieces of the past clinical data are stored in advance, selects similar clinical data which is similar to the distribution pattern among the pieces of clinical data, and displays the similar clinical data on the display unit. For example, the similar clinical data selection unit displays an oxygen saturation image included in the similar clinical data on the display unit.

In addition, the endoscope system may further include a therapeutic effect score calculation unit. The therapeutic effect score calculation unit calculates a therapeutic effect score, which indicates a therapeutic effect of a specific treatment method, based on the distribution pattern, and displays the therapeutic effect score on the display unit.

In addition, the endoscope system may further include an autosave control unit. For example, even if a freeze operation for storing a still image of the observation target is not performed, in a case in which the disease state score is a value equal to or greater than a specified value, the autosave control unit associates the disease state score with an oxygen saturation image generated based on the image signal and the oxygen saturation and automatically stores them.

The display unit may display the disease state score or information based on the disease state score in a case in which the disease state score is equal to or greater than a specific value.

In addition, it is preferable that the endoscope system of the present invention further includes a feature region extraction unit that extracts a feature region of the observation target based on the image signal. In this case, the disease state score calculation unit calculates the disease state score based on the distribution pattern of the oxygen saturation in the feature region.

For example, the feature region extraction unit extracts the feature region of the observation target based on a blue image signal obtained from a blue pixel of the image sensor or a green image signal obtained from a green pixel of the image sensor.

The feature region is a rubor region, and it is preferable that the disease state score in a case in which a high oxygen region having the oxygen saturation equal to or greater than a predetermined value is present in the rubor region is greater than the disease state score in a case in which the high oxygen region is not present in the rubor region. In addition, it is preferable that, in a case in which the high oxygen region is present in the rubor region, the disease state score increases as a proportion of the high oxygen region with respect to the rubor region increases.

The feature region may be a rubor region, and the disease state score in a case in which a high oxygen region having the oxygen saturation equal to or greater than a predetermined value is present in the rubor region may be smaller than the disease state score in a case in which the high oxygen region is not present in the rubor region. In this case, in a case in which the high oxygen region is present in the rubor region, the disease state score may decrease as a proportion of the high oxygen region with respect to the rubor region increases.

A message display control unit that monitors the disease state score and displays a message corresponding to the disease state score on the display unit may be provided.

A processor device for an endoscope system of the present invention is a processor device for an endoscope system including a light source device for emitting light to irradiate an observation target, an image sensor for imaging the observation target with reflected light of the light emitted from the light source device and outputting an image signal, and a display unit, and includes an oxygen saturation calculation unit, a distribution pattern generation unit, and a disease state score calculation unit. The oxygen saturation calculation unit calculates an oxygen saturation of the observation target based on the image signal. The distribution pattern generation unit generates a distribution pattern showing a distribution of the oxygen saturation. The disease state score calculation unit calculates a disease state score indicating a disease state of the observation target based on the distribution pattern.

In addition, a feature region extraction unit that extracts a feature region of the observation target based on the image signal may be provided. In this case, the disease state score calculation unit calculates the disease state score based on the distribution pattern of the oxygen saturation in the feature region.

An operation method for an endoscope system of the present invention is an operation method for an endoscope system including a light source device for emitting light to irradiate an observation target, an image sensor for imaging the observation target with reflected light of the light emitted from the light source device and outputting an image signal, and a display unit, and includes an oxygen saturation calculation step, a distribution pattern generation step, a disease state score calculation step, and a display step. In the oxygen saturation calculation step, the oxygen saturation calculation unit calculates an oxygen saturation of the observation target based on the image signal. In the distribution pattern generation step, the distribution pattern generation unit generates a distribution pattern showing a distribution of the oxygen saturation. In the disease state score calculation step, the disease state score calculation unit calculates a disease state score indicating a disease state of the observation target based on the distribution pattern. In the display step, the display unit displays the disease state score or information based on the disease state score.

In addition, a feature region extraction step may be included in which the feature region extraction unit extracts a feature region of the observation target based on the image signal. In this case, in the disease state score calculation step, the disease state score calculation unit calculates the disease state score based on the distribution pattern of the oxygen saturation in the feature region.

An operation method for a processor device of the present invention is an operation method for a processor device for processing an image signal obtained by imaging an observation target, and includes an oxygen saturation calculation step, a distribution pattern generation step, and a disease state score calculation step. In the oxygen saturation calculation step, the oxygen saturation calculation unit calculates an oxygen saturation of the observation target based on the image signal. In the distribution pattern generation step, the distribution pattern generation unit generates a distribution pattern showing a distribution of the oxygen saturation. In the disease state score calculation step, the disease state score calculation unit calculates a disease state score indicating a disease state of the observation target based on the distribution pattern.

In addition, a feature region extraction step may be included in which the feature region extraction unit extracts a feature region of the observation target based on the image signal. In this case, in the disease state score calculation step, the disease state score calculation unit calculates the disease state score based on the distribution pattern of the oxygen saturation in the feature region.

According to the endoscope system, the processor device for an endoscope system, the operation method for an endoscope system, and the operation method for a processor device of the present invention, it is possible to further present information for assisting the doctor in performing more accurate and detailed diagnosis based on the oxygen saturation.

DESCRIPTION OF THE PREFERRED EMBODIMENTS

[First Embodiment]

Figure 1:
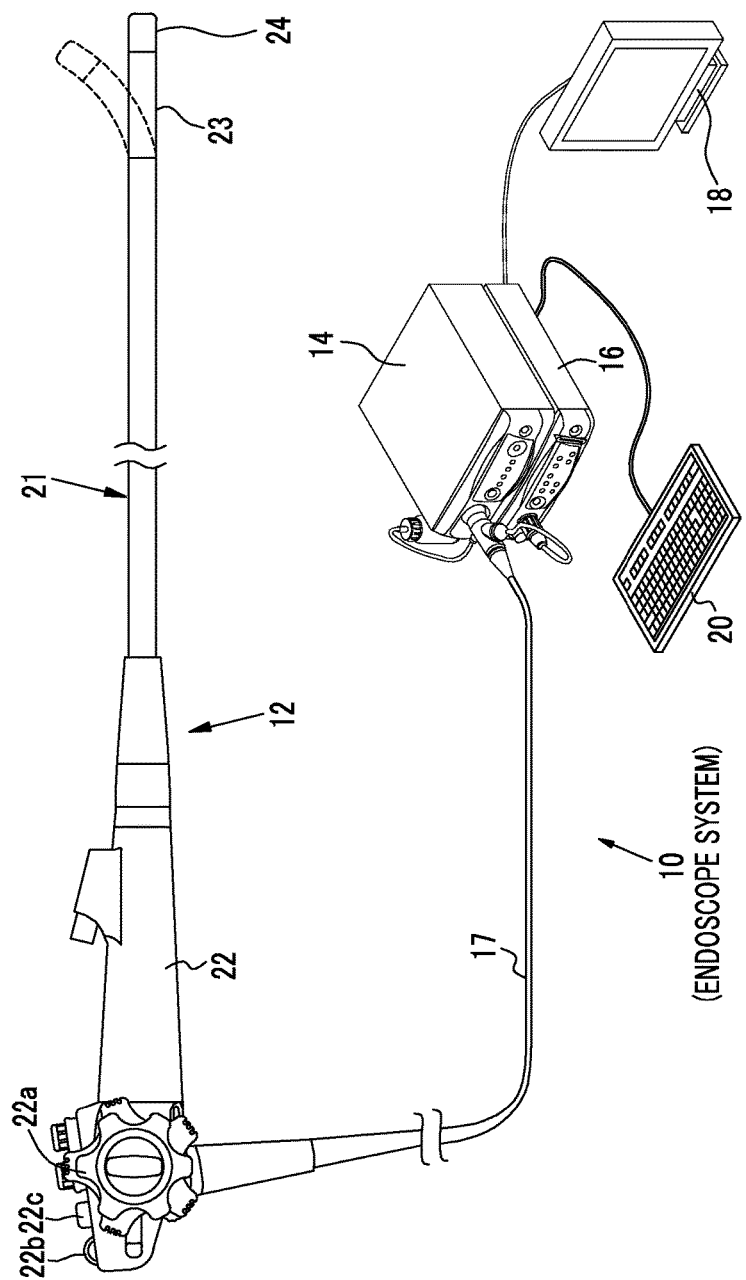
FIG. 1 is an external view of an endoscope system.

As shown in FIG. 1, an endoscope system 10 of a first embodiment includes an endoscope 12, a light source device 14, a processor device 16, a monitor 18 (display unit), and a console 20. The endoscope 12 is optically connected to the light source device 14, and is electrically connected to the processor device 16. The endoscope 12 includes an insertion unit 21 that is inserted into a subject, an operation unit 22 provided at the proximal end of the insertion unit 21, and a bending portion 23 and a distal portion 24 that are provided at the distal side of the insertion unit 21. By operating an angle knob 22a of the operation unit 22, the bending portion 23 is bent. Through the bending operation, the distal portion 24 is directed toward a desired direction.

In addition to the angle knob 22a, a mode selector SW (mode selector switch) 22b, a zoom operation unit 22c, and a freeze button (not shown) for saving a still image are provided in the operation unit 22. The mode selector SW 22b is used for a switching operation between two modes of a normal observation mode and a special observation mode. The normal observation mode is a mode in which a normal light image obtained by full-color imaging of the observation target in the subject is displayed on the monitor 18. The special observation mode is a mode in which an oxygen saturation image obtained by imaging the oxygen saturation of blood hemoglobin of the observation target is displayed on the monitor 18. The zoom operation unit 22c is used for a zooming operation for driving a zoom lens 47 (refer to FIG. 2) in the endoscope 12 in order to magnify the observation target.

The processor device 16 is electrically connected to the monitor 18 and the console 20. The monitor 18 displays an image, such as a normal light image or an oxygen saturation image, and information regarding these images (hereinafter, referred to as image information or the like). The console 20 functions as a user interface (UI) for receiving an input operation, such as a function setting. In addition, a recording unit (not shown) in which image information or the like is recorded may be connected to the processor device 16.

Figure 2:
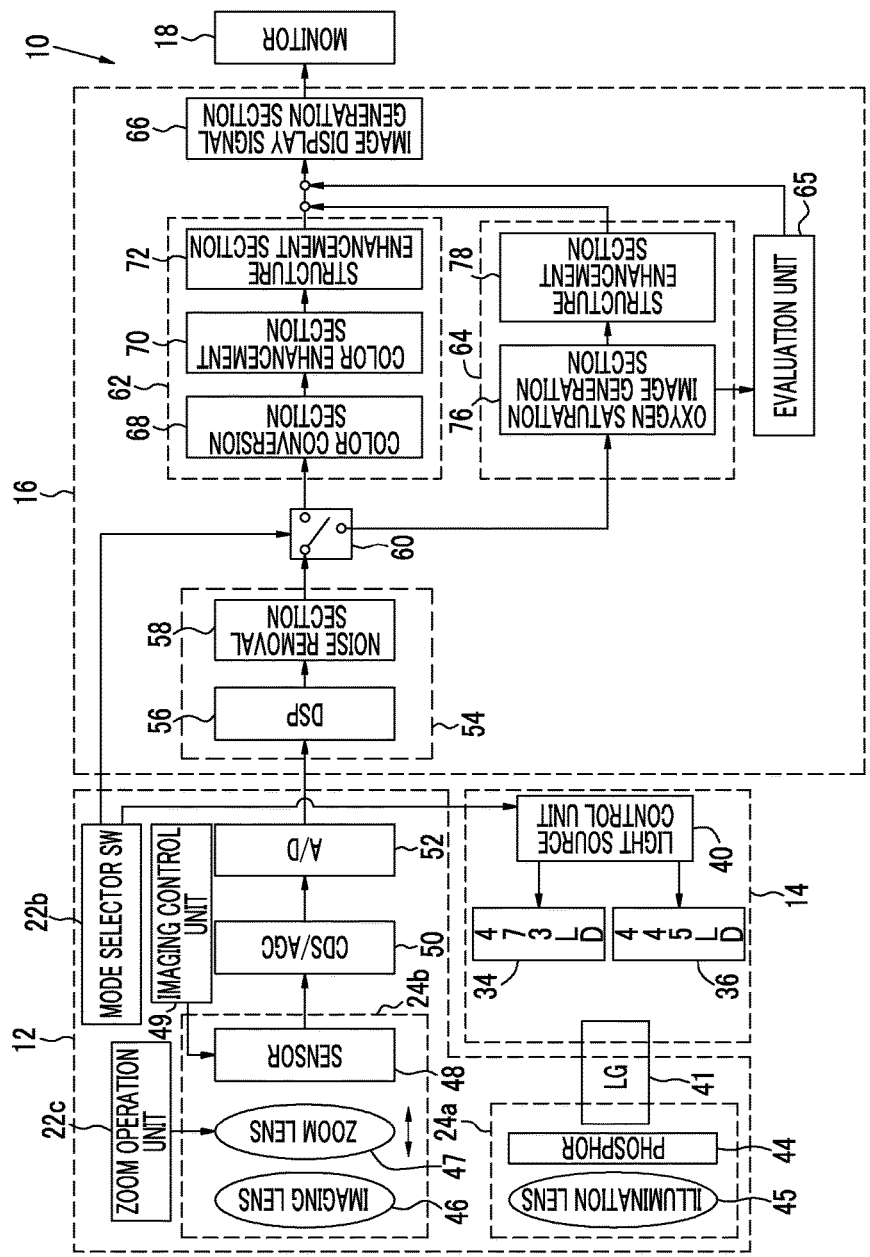
FIG. 2 is a block diagram of the endoscope system.

As shown in FIG. 2, the light source device 14 includes, as light emitting sources, a first blue laser light source (473 LD (laser diode)) 34 that emits first blue laser light having a center wavelength of 473 nm and a second blue laser light source (445 LD) 36 that emits second blue laser light having a center wavelength of 445 nm. Emission of the light sources 34 and 36 formed of semiconductor light emitting devices are separately controlled by a light source control unit 40. Therefore, the light amount ratio between light emitted from the first blue laser light source 34 and light emitted from the second blue laser light source 36 can be freely changed.

The light source control unit 40 turns on the second blue laser light source 36 in the normal observation mode. On the other hand, in the special observation mode, the first blue laser light source 34 and the second blue laser light source 36 are alternately turned on at intervals of one frame. In addition, it is preferable that the half-width of each of the first and second blue laser light beams is set to approximately ±10 nm. As the first blue laser light source 34 and the second blue laser light source 36, a broad area type InGaN-based laser diode can be used, or an InGaNAs-based laser diode or a GaNAs-based laser diode can be used. In addition, as the above light sources, a structure using a light emitter, such as a light emitting diode, may be used.

The first and second blue laser light beams emitted from the light sources 34 and 36 are incident into a light guide (LG) 41 through optical members, such as a collecting lens, an optical fiber, and a multiplexer (none are shown). The light guide 41 is built into a universal cord 17 that connects the endoscope 12 and the light source device 14 to each other (refer to FIG. 1) and the endoscope 12. The light guide 41 propagates the first and second blue laser light beams from the light sources 34 and 36 to the distal portion 24 of the endoscope 12 therethrough. As the light guide 41, a multi-mode fiber may be used. As an example, it is possible to use a small-diameter fiber cable having a diameter of ϕ0.3 mm to ϕ0.5 mm that includes a core with a diameter of 105 μm, cladding with a diameter of 125 μm, and a protective layer as an outer skin.

The distal portion 24 of the endoscope 12 includes an illumination optical system 24a and an imaging optical system 24b. A phosphor 44 and an illumination lens 45 are provided in the illumination optical system 24a. The first and second blue laser light beams are incident on the phosphor 44 from the light guide 41. The phosphor 44 emits fluorescence due to the first or second blue laser light irradiating thereto. Some of the first or second blue laser light transmits through the phosphor 44. The light emitted from the phosphor 44 is emitted to irradiate the observation target through the illumination lens 45.

Figure 3:
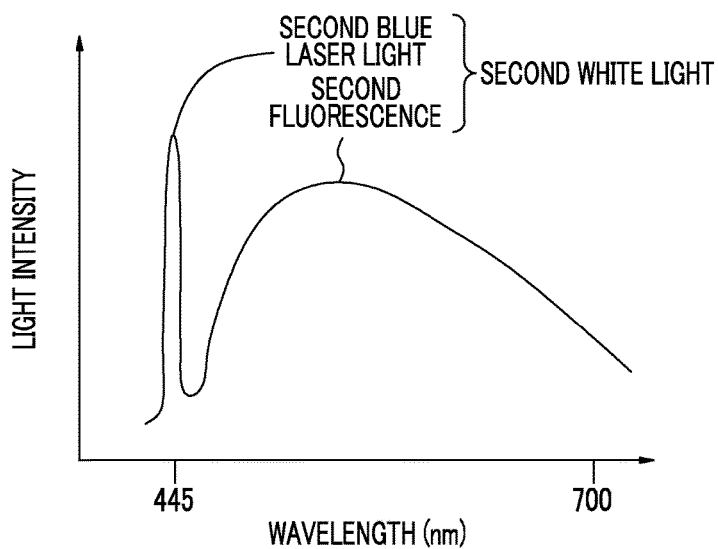
FIG. 3 is a graph showing the spectrum of light emitted in a normal observation mode.

In the normal observation mode, the second blue laser light is incident on the phosphor 44. Accordingly, white light having a spectrum shown in FIG. 3 (second white light) is emitted to irradiate the observation target as illumination light. The second white light includes second blue laser light and second fluorescence of green to red that is excited and emitted from the phosphor 44 by the second blue laser light. Accordingly, the wavelength range of the second white light covers the entire visible light region.

Figure 4:
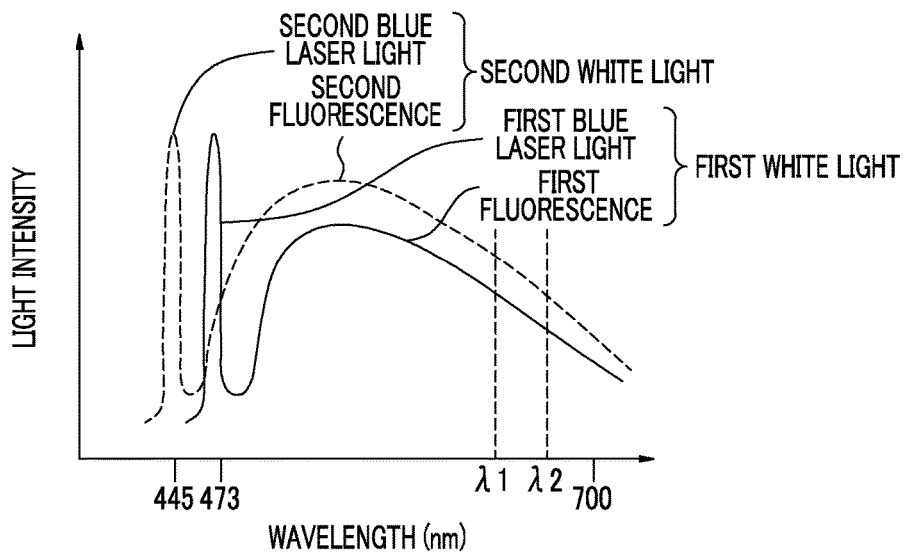
FIG. 4 is a graph showing the spectrum of light emitted in a special observation mode.

On the other hand, in the special observation mode, the first blue laser light and the second blue laser light are alternately incident on the phosphor 44. Therefore, first white light and second white light having the spectrums shown in FIG. 4 are alternately emitted to the observation target. The first white light is configured to include first blue laser light and first fluorescence of green to red that is excited and emitted from the phosphor 44 by the first blue laser light. Accordingly, the wavelength range of the first white light covers the entire visible light region. The second white light is the same as the second white light emitted in the normal observation mode.

The first fluorescence and the second fluorescence have almost the same waveform (shape of the spectrum), and the ratio between the intensity (I1 (λ)) of the first fluorescence and the intensity (I2 (λ)) of the second fluorescence (hereinafter, referred to as an inter-frame intensity ratio) is the same at any wavelength λ. For example, it is I2 (λ1)/I1 (λ1)=I2 (λ2)/I1 (λ2). Since the inter-frame intensity ratio I2 (λ)/I1 (λ) affects the calculation accuracy of the oxygen saturation, the inter-frame intensity ratio I2 (λ)/I1 (λ) is accurately controlled by the light source control unit 40 such that the reference inter-frame intensity ratio set in advance is maintained.

As the phosphor 44, it is preferable to use a phosphor that absorbs some of the first and second blue laser light and includes a plurality of kinds of phosphors (for example, a YAG-based phosphor or a phosphor, such as BAM ($BaMgAl_{10}O_{17}$)) that are excited to emit green to red light beams. In a case that a semiconductor light emitting device is used as a light source for exciting the phosphor 44 as in the present embodiment, it is possible to obtain high-intensity first and second white light beams with high luminous efficiency. In addition, it is possible to easily adjust the intensity of the white light and to suppress changes in color temperature and chromaticity.

The imaging optical system 24b of the endoscope 12 includes an imaging lens 46, the zoom lens 47, and a sensor 48 (refer to FIG. 2). Reflected light from the observation target is incident on the sensor 48 through the imaging lens 46 and the zoom lens 47. Then, a reflected image of the observation target is formed on the sensor 48. The zoom lens 47 is moved between the tele end and the wide end by operating the zoom operation unit 22c. When the zoom lens 47 is moved to the tele end side, the reflected image of the observation target is magnified. On the other hand, when the zoom lens 47 is moved to the wide end side, the reflected image of the observation target is reduced. In addition, in a case in which magnified observation is not performed (at the time of non-magnified observation), the zoom lens 47 is disposed at the wide end. In case of performing magnified observation, the zoom lens 47 is moved from the wide end to the tele end side by operating the zoom operation unit 22c.

The sensor 48 is a color imaging device, and captures a reflected image of the observation target and outputs the image signal. For example, the sensor 48 is a charge coupled device (CCD) image sensor or a complementary metal oxide semiconductor (CMOS) image sensor. In addition, the sensor 48 includes RGB pixels in which RGB color filters are provided on the imaging surface, and outputs image signals of three colors of R, and B by performing photoelectric conversion in the pixels of respective colors of RGB.

Figure 5:
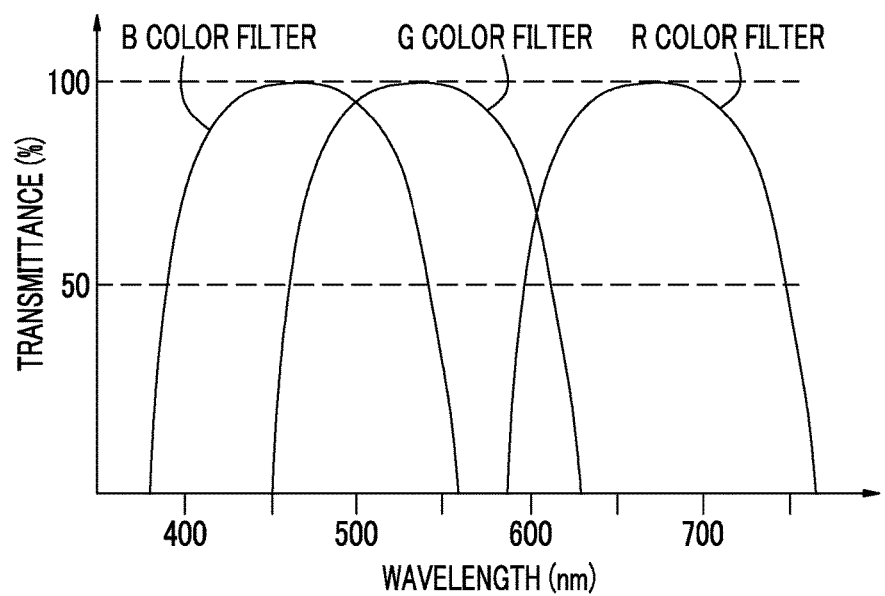
FIG. 5 is a graph showing the spectral transmittance of an RGB color filter.

As shown in FIG. 5, the B color filter has a spectral transmittance of 380 nm to 560 nm, the G color filter has a spectral transmittance of 450 nm to 630 nm, and the R color filter has a spectral transmittance of 580 nm to 760 nm. Accordingly, in a case in which the second white light is emitted to irradiate the observation target in the normal observation mode, the second blue laser light and some of green components of the second fluorescence are incident on the B pixel, some of green components of the second fluorescence are incident on the G pixel, and red components of the second fluorescence are incident on the R pixel. However, since the emission intensity of the second blue laser light is extremely greater than that of the second fluorescence, most of the B image signal output from the B pixel is occupied by the reflected light components of the second blue laser light.

On the other hand, in a case in which the first white light is emitted to irradiate the observation target in the special observation mode, the first blue laser light and some of green components of the first fluorescence are incident on the B pixel, some of green components of the first fluorescence are incident on the G pixel, and red components of the first fluorescence are incident on the R pixel. However, since the emission intensity of the first blue laser light is extremely greater than that of the first fluorescence, most of the B image signal is occupied by the reflected light components of the first blue laser light. Light incidence components in the respective RGB pixels when the second white light is emitted to the observation target in the special observation mode are the same as those in the normal observation mode.

As the sensor 48, it is also possible to use a so-called complementary color image sensor including complementary color filters of cyan (C), magenta (M), yellow (Y), and green (G) on the imaging surface. In case of using the complementary color image sensor as the sensor 48, a color converter that performs color conversion from image signals of four colors of CMYG to image signals of three colors of RGB is preferably provided in the endoscope 12, the light source device 14, or the processor device 16. In this manner, even in a case in which complementary color image sensors are used, it is possible to obtain the image signals of three colors of RGB from the image signals of four colors of CMYG by color conversion.

Figure 6:
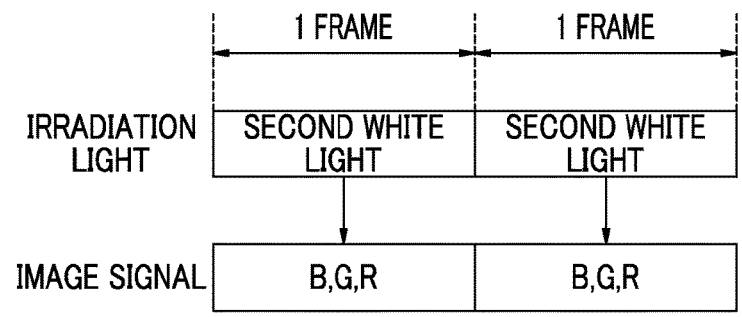
FIG. 6 is an explanatory diagram showing imaging control in the normal observation mode.

An imaging control unit 49 controls the imaging of the sensor 48. As shown in FIG. 6, in the normal observation mode, an observation target illuminated with the second white light is imaged by the sensor 48 for each period of one frame. Then, the image signals of RGB are output from the sensor 48 for each frame.

Figure 7:
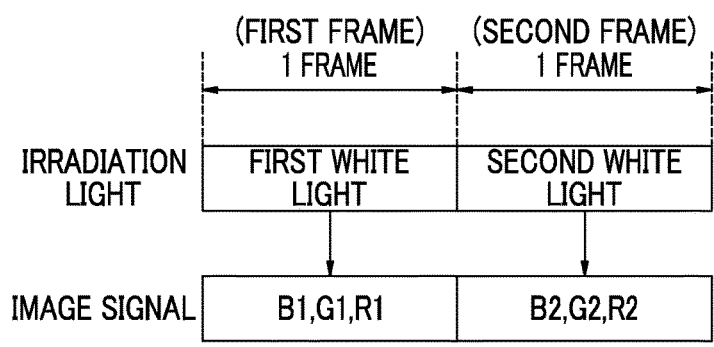
FIG. 7 is an explanatory diagram showing imaging control in the special observation mode.

Also in the special observation mode, the imaging control unit 49 performs imaging control of the sensor 48 in the same manner as in the normal observation mode. However, in the special observation mode, the first white light and the second white light are alternately emitted to the observation target in synchronization with the imaging frames of the sensor 48. Therefore, as shown in FIG. 7, the sensor 48 images the observation target with the first white light in the first frame, and images the observation target with the second white light in the next second frame. The sensor 48 outputs the image signals of RGB colors in both the first and second frames. However, the spectrum of white light in the first frame and the spectrum of white light in the second frame are different. Therefore, for the sake of distinction, the image signals of RGB colors obtained by imaging the observation target with the first white light in the first frame are referred to as an R1 image signal, a G1 image signal, and a B1 image signal, and the image signals of RGB colors obtained by imaging the observation target with the second white light in the second frame are referred to as an R2 image signal, a G2 image signal, and a B2 image signal.

In order to calculate the oxygen saturation, a signal ratio B1/G2 between the B1 image signal and the G2 image signal and a signal ratio R2/G2 between the R2 image signal and the G2 image signal are used. Between these signal ratios, the signal ratio B1/G2 between the B1 image signal and the G2 image signal is an essential signal ratio for the calculation of the oxygen saturation. In the present embodiment, therefore, a component (first blue laser light transmitted through the phosphor 44) that becomes the B1 image signal in the first white light is the first signal light, and a component (green band component of the second fluorescence) that becomes the G2 image signal in the second white light is the second signal light.

The image signals of the respective colors output from the sensor 48 are transmitted to a correlated double sampling (CDS)/automatic gain control (AGC) circuit 50 (refer to FIG. 2). The CDS/AGC circuit 50 performs correlated double sampling (CDS) or automatic gain control (AGC) for the analog image signals output from the sensor 48. The image signals transmitted through the CDS/AGC circuit 50 are converted into digital image signals by an A/D converter 52. The image signals that have been digitized in this manner are input to the processor device 16.

The processor device 16 includes a receiving unit 54, an image processing switching unit 60, a normal observation image processing unit 62, a special observation image processing unit 64, an evaluation unit 65, and an image display signal generation unit 66. The receiving unit 54 receives the image signal input from the endoscope 12. The receiving unit 54 includes a digital signal processor (DSP) 56 and a noise removal section 58, and the DSP 56 performs digital signal processing, such as color correction processing, on the received image signal. The noise removal section 58 performs noise removal processing using, for example, a moving average method or a median filter method, on the image signal obtained after the color correction processing or the like in the DSP 56. The image signals after noise has been removed are input to the image processing switching unit 60.

In a case in which the mode selector SW 22b is set to the normal observation mode, the image processing switching unit 60 inputs the image signals to the normal observation image processing unit 62. On the other hand, in a case in which the mode selector SW 22b is set to the special observation mode, the image processing switching unit 60 inputs the image signals to the special observation image processing unit 64.

The normal observation image processing unit 62 includes a color conversion section 68, a color enhancement section 70, and a structure enhancement section 72. The color conversion section 68 generates RGB image data by assigning the input RGB image signals of one frame to R, and B pixels. Then, color conversion processing, such as 3×3 matrix processing, gradation conversion processing, and three-dimensional LUT processing, is performed on the RGB image data.

The color enhancement section 70 performs various kinds of color enhancement processing on the RGB image data after the color conversion processing. The structure enhancement section 72 performs structure enhancement processing, such as spatial frequency enhancement, on the RGB image data after the color enhancement processing. The RGB image data subjected to the structure enhancement processing by the structure enhancement section 72 is input to the image display signal generation unit 66 as a normal observation image.

The special observation image processing unit 64 includes an oxygen saturation image generation section 76 and a structure enhancement section 78. The oxygen saturation image generation section 76 calculates an oxygen saturation, and generates an oxygen saturation image indicating the calculated oxygen saturation.

The structure enhancement section 78 performs structure enhancement processing, such as spatial frequency enhancement processing, on the oxygen saturation image input from the oxygen saturation image generation section 76. The oxygen saturation image subjected to the structure enhancement processing by the structure enhancement section 78 is input to the image display signal generation unit 66.

The evaluation unit 65 acquires the data of the oxygen saturation calculated by the oxygen saturation image generation section 76, and generates a distribution pattern showing the distribution regarding the oxygen saturation based on the data of the oxygen saturation. Then, based on the calculated distribution pattern, a disease state score indicating the state of disease of the observation target is calculated. The state of disease is, for example, the degree of progression of cancer.

The image display signal generation unit 66 converts the normal observation image or the oxygen saturation image into a display format signal (display image signal), and inputs the display format signal to the monitor 18. As a result, the normal observation image or the oxygen saturation image is displayed on the monitor 18. In addition, a disease state score is input to the image display signal generation unit 66 from the evaluation unit 65. Accordingly, the image display signal generation unit 66 displays not only the oxygen saturation image but also the "disease state score" or "information based on the disease state score (warning message or the like)" on the monitor 18. Therefore, a doctor can diagnose a tissue, which may be a lesion, more objectively and accurately and in detail by referring to not only the oxygen saturation image but also the display of the "disease state score" or the "information based on the disease state score".

Figure 8:
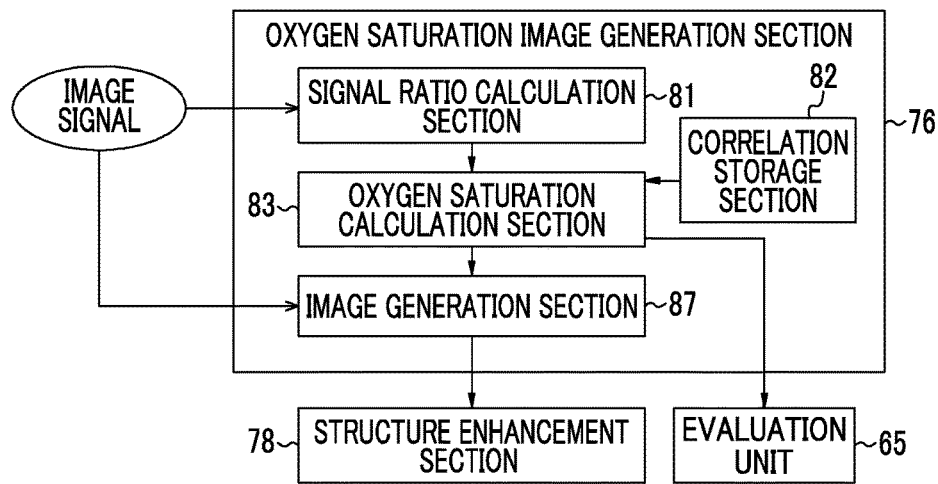
FIG. 8 is a block diagram of an oxygen saturation image generation section.

As shown in FIG. 8, the oxygen saturation image generation section 76 includes a signal ratio calculation section 81, a correlation storage section 82, an oxygen saturation calculation section 83, and an image generation section 87.

Among the image signals of two frames that are input to the oxygen saturation image generation section 76, the B1 image signal, the G2 image signal, and the R2 image signal are input to the signal ratio calculation section 81. The signal ratio calculation section 81 calculates the signal ratios B1/G2 between the B1 image signal and the G2 image signal and the signal ratio R2/G2 between the G2 image signal and the R2 image signal for each pixel.

Figure 9:
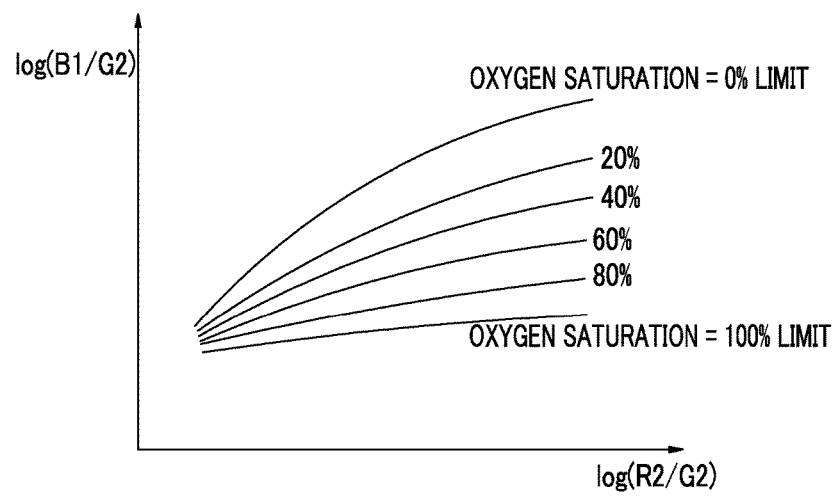
FIG. 9 is a graph showing the correlation between the signal ratios B1/G2 and R2/G2 and the oxygen saturation.

The correlation storage section 82 stores the correlation between the signal ratios B1/G2 and R2/G2 and the oxygen saturation. This correlation is stored in a two-dimensional table that defines the isolines of the oxygen saturation on the two-dimensional space shown in FIG. 9. The position and shape of the isolines for the signal ratios B1/G2 and R2/G2 are obtained in advance by physical simulation of light scattering, and the distance between the isolines changes according to the blood volume (signal ratio R2/G2). In addition, the correlation between the signal ratios B1/G2 and R2/G2 and the oxygen saturation is stored in a log scale.

Figure 10:
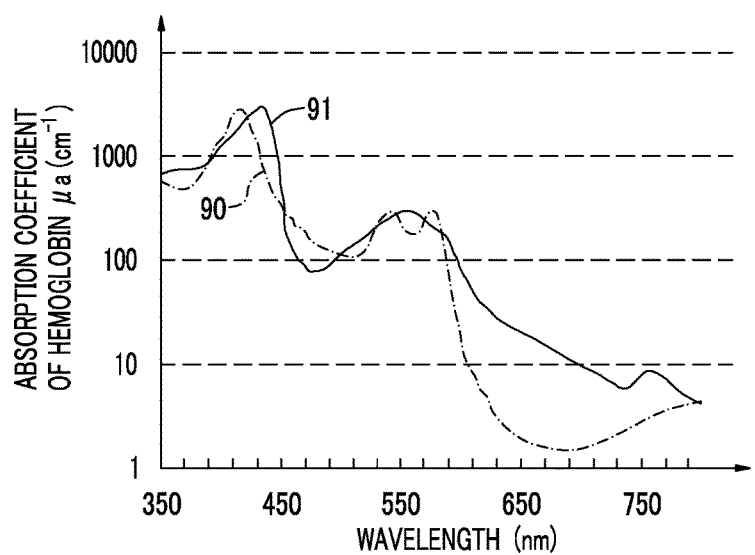
FIG. 10 is a graph showing the absorption coefficients of oxygenated hemoglobin and reduced hemoglobin.

As shown in FIG. 10, this correlation is closely related to the absorption characteristics or light scattering characteristics of oxygenated hemoglobin (graph 90) and reduced hemoglobin (graph 91). For example, as at a center wavelength of 473 nm of the first blue laser light, at a wavelength at which the difference between the absorption coefficient of oxygenated hemoglobin and the absorption coefficient of reduced hemoglobin is large, it is easy to handle the information of the oxygen saturation. However, the B1 image signal including a signal corresponding to 473 nm light has a high dependence not only on the oxygen saturation but also on the blood volume. Therefore, by using not only the B1 image signal but also the signal ratios B1/G2 and R2/G2 obtained from the R2 image signal, which corresponds to light that changes mainly depending on the blood volume, and the G2 image signal, which is a reference signal of the B1 image signal and the R2 image signal, it is possible to accurately calculate the oxygen saturation without dependency on the blood volume.

Figure 11:
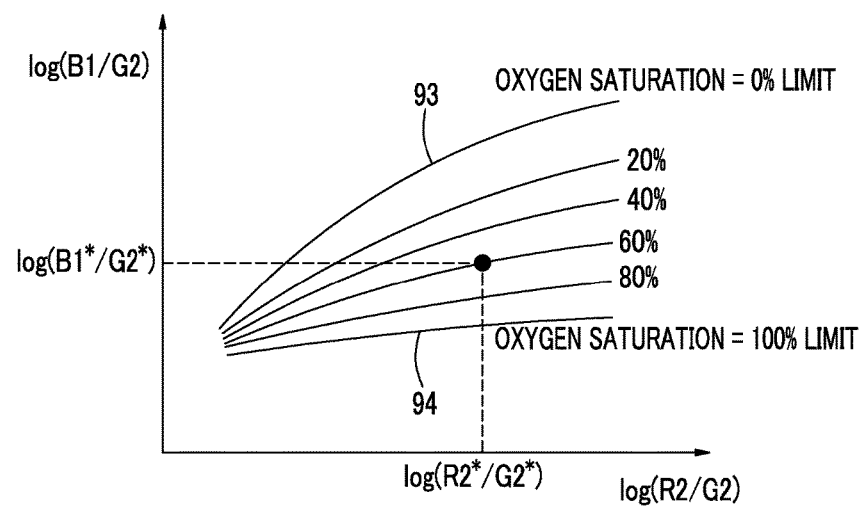
FIG. 11 is an explanatory diagram showing a method of calculating the oxygen saturation.

The oxygen saturation calculation section 83 calculates an oxygen saturation corresponding to the signal ratio B1/G2 and the signal ratio R2/G2 calculated by the signal ratio calculation section 81, for each pixel, with reference to the correlation stored in the correlation storage section 82. For example, in a case in which the signal ratio B1/G2 and the signal ratio R2/G2 in a specific pixel are B1*/G2* and R2*/G2*, respectively, the oxygen saturation corresponding to the signal ratio B1*/G2* and the signal ratio R2*/G2* is "60%" when the correlation shown in FIG. 11 is referred to. Accordingly, the oxygen saturation calculation section 83 calculates the oxygen saturation of the pixel as "60%".

In addition, a case in which the signal ratio B1/G2 and the signal ratio R2/G2 become extremely large or extremely small hardly occurs. That is, a case hardly occurs in which the value of the signal ratio B1/G2 or the signal ratio R2/G2 exceeds the lower limit line 93 of the oxygen saturation of 0% or on the contrary becomes lower than the upper limit line 94 of the oxygen saturation of 100%. Here, the oxygen saturation calculation section 83 sets the oxygen saturation to 0% in a case in which the calculated oxygen saturation is lower than the lower limit line 93, and sets the oxygen saturation to 100% in a case in which the calculated oxygen saturation exceeds the upper limit line 94. In addition, in a case in which a point corresponding to the signal ratio B1/G2 and the signal ratio R2/G2 deviates from a region between the lower limit line 93 and the upper limit line 94, display showing that the reliability of the oxygen saturation in the pixel is low may be given, or the oxygen saturation may not be calculated.

The image generation section 87 generates an oxygen saturation image, which is obtained by imaging the oxygen saturation, using the data of the oxygen saturation calculated by the oxygen saturation calculation section 83, the B2 image signal, the G2 image signal, and the R2 image signal. Specifically, the image generation section 87 applies a gain corresponding to the oxygen saturation to the original B2 image signal, G2 image signal, and R2 image signal, which have been input, for each pixel, and generates RGB image data using the B2 image signal, the G2 image signal, and the R2 image signal after applying the gain. For example, in a pixel where the corrected oxygen saturation is 60% or more, the image generation section 87 multiplies all of the B2 image signal, the G2 image signal, and the R2 image signal by the same gain "1". In contrast, in a pixel where the corrected oxygen saturation is less than 60%, the image generation section 87 multiplies the B2 image signal by the gain less than "1" and multiplies the G2 image signal and the R2 image signal by the gain of "1" or more. RGB image data generated using the B1 image signal, the G2 image signal, and the R2 image signal after the gain processing is an oxygen saturation image.

In the oxygen saturation image generated by the image generation section 87, a high oxygen region (region having an oxygen saturation of 60% to 100%) is expressed in the same color as the normal observation image. On the other hand, a low oxygen region where the oxygen saturation is less than a specific value (region having an oxygen saturation of 0% to 60%) is expressed in a different color (pseudocolor) from the normal observation image.

Although the image generation section 87 performs gain multiplication for pseudo-coloring of only the low oxygen region in the present embodiment, a gain corresponding to the oxygen saturation may also be multiplied for the high oxygen region so that the entire oxygen saturation image is pseudo-colored. In addition, although the low oxygen region and the high oxygen region are divided at the oxygen saturation of 60%, this boundary can be arbitrarily selected.

Figure 12:
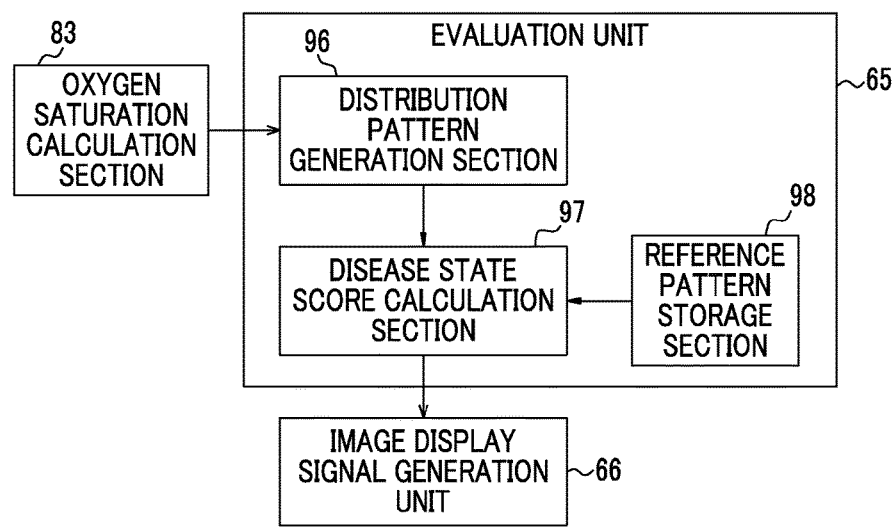
FIG. 12 is a block diagram showing an evaluation unit.

As shown in FIG. 12, the evaluation unit 65 includes a distribution pattern generation section 96, a disease state score calculation section 97, and a reference pattern storage section 98.

The distribution pattern generation section 96 acquires the data of oxygen saturation calculated for each pixel by the oxygen saturation calculation section 83, and generates a distribution pattern showing the distribution regarding the oxygen saturation. For example, the distribution pattern is a two-dimensional distribution pattern in which the oxygen saturation of each pixel is arranged as an image, a distribution pattern regarding the inclination of the oxygen saturation obtained by differentiating this in a predetermined direction, or a spatial frequency spectrum obtained by performing a Fourier transform of the two-dimensional distribution pattern in which the oxygen saturation of each pixel is arranged as an image. In the present embodiment, the distribution pattern generation section 96 calculates the distribution of oxygen saturation as a distribution pattern. However, the distribution pattern generation section 96 may generate other distribution patterns described above, or may generate a plurality of distribution patterns.

Figure 13:
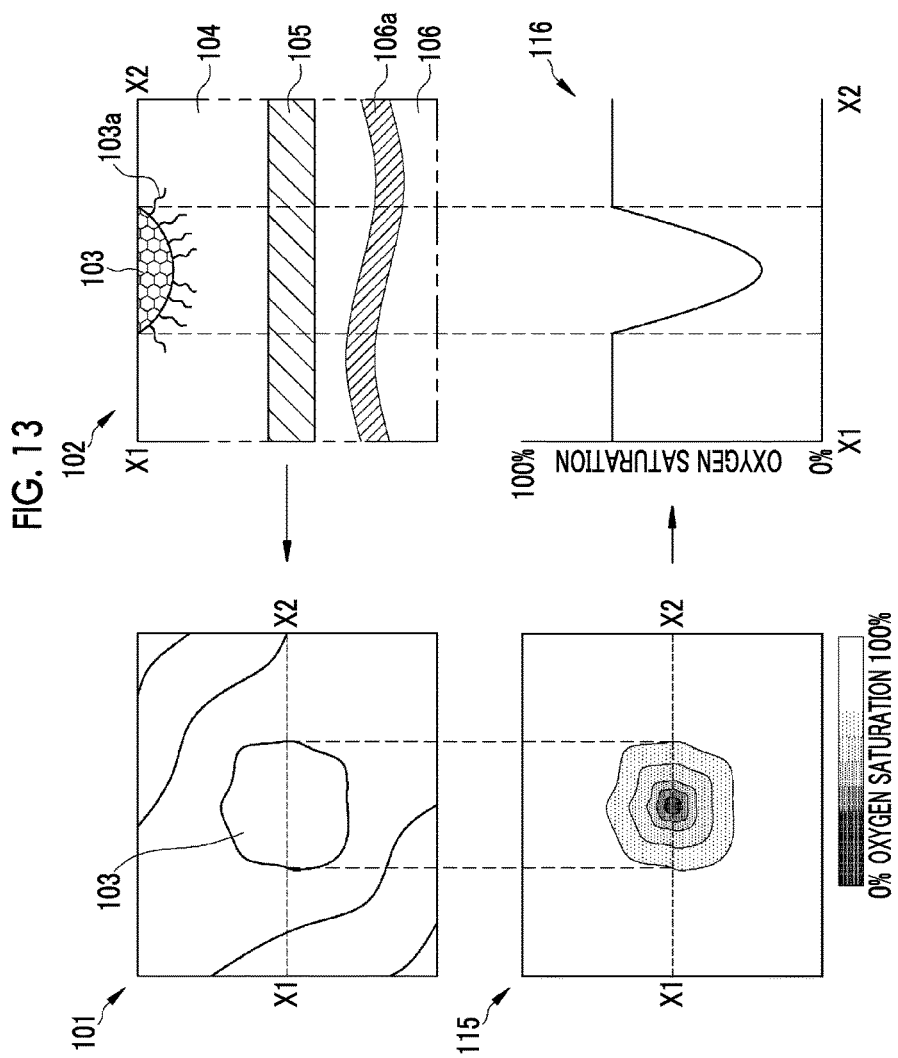
FIG. 13 is an explanatory diagram showing a section of early cancer, a normal observation image, and oxygen saturation.

For example, as shown in a normal observation image 101 and a section 102 of the center in FIG. 13, in the case of early cancer in which a cancer tissue 103 remains in a mucosal layer 104 without infiltrating into a muscularis mucosa 105, new blood vessels 103a are constructed around the cancer tissue 103, but the new blood vessels 103a do not reach a thick blood vessel 106a in a submucosal tissue layer 106. Therefore, as shown in a distribution 115 of the oxygen saturation or a distribution 116 in the center, the cancer tissue 103 is a low oxygen region having a lower oxygen saturation than the normal tissue. In a part having a higher percentage of cancer tissue, the oxygen saturation is lower because oxygen is deficient. Accordingly, in early cancer, the lowest oxygen state occurs approximately near the center of the cancer tissue 103. For this reason, when viewed along the X1-X2 section of the center, the distribution of oxygen saturation is a U-shaped (or V-shaped) distribution.

Figure 14:
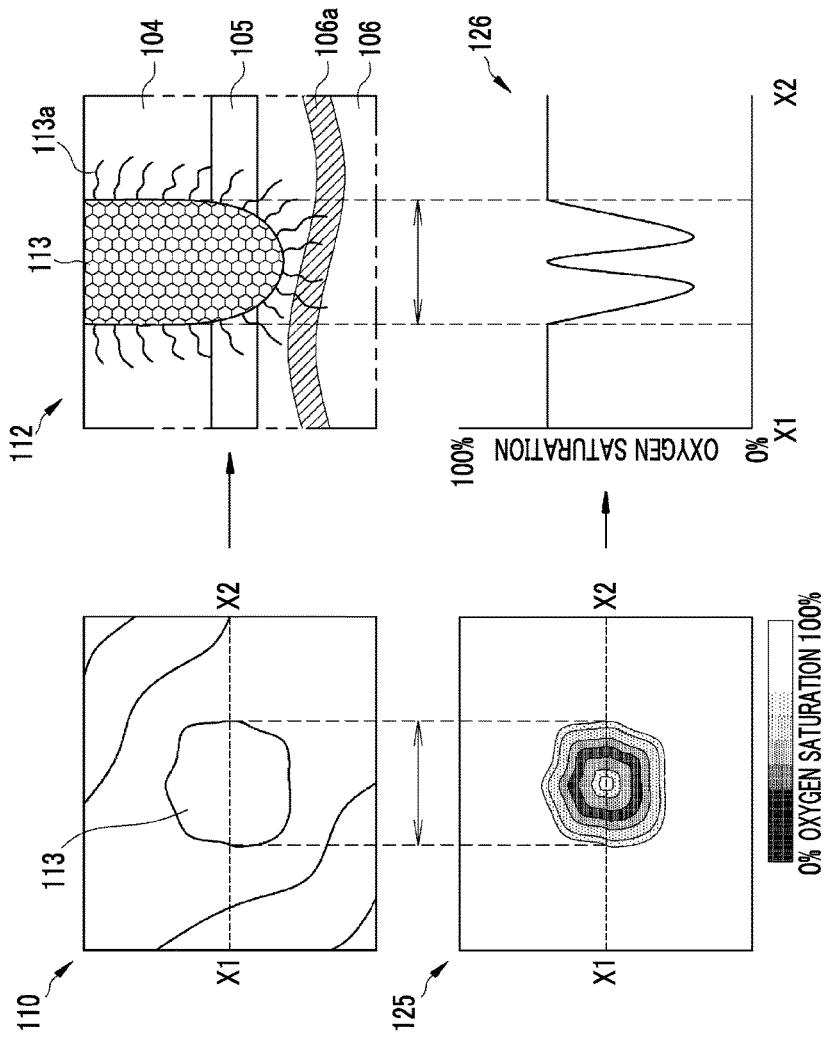
FIG. 14 is an explanatory diagram showing a section of advanced cancer, a normal observation image, and oxygen saturation.

On the other hand, as shown in a normal observation image 110 or a section 112 of the center in FIG. 14, in the case of advanced cancer having a cancer tissue 113 that has infiltrated into the muscularis mucosa 105, some of new blood vessels 113a constructed around the cancer tissue 113 reach the thick blood vessel 106a in the submucosal tissue layer 106. Therefore, as shown in a distribution 125 of oxygen saturation or a distribution 126 in the center, in a peripheral portion of the cancer tissue 113 having the new blood vessels 113a that do not reach the thick blood vessel 106a of the submucosal tissue layer 106, a low oxygen state occurs in which the oxygen saturation is lower than surrounding normal tissues, similar to the cancer tissue 103 that is early cancer. However, in a central portion having the new blood vessels 113a that reach the thick blood vessel 106a of the submucosal tissue layer 106, a high oxygen state approximately equal to, for example, normal tissues occurs since the supply of oxygen is abundant. For this reason, in advanced cancer, a high oxygen region is formed in a central portion, and an annular low oxygen region is observed in which a portion around the central portion is surrounded by a low oxygen region. In addition, when viewed along the X1-X2 section of the center, the distribution of oxygen saturation is a distribution close to a W shape having a convex center.

In the present embodiment, the distribution pattern generation section 96 calculates the distributions 115 and 125 of oxygen saturation as distribution patterns. The inclination or the spatial frequency spectrum of oxygen saturation can be calculated by differentiating the distributions 115 and 125 of oxygen saturation or by performing a Fourier transform. As can be seen from FIGS. 13 and 14, in case that cancer is generated, a high frequency component is generated in the spatial frequency spectrum of the oxygen saturation. And in a case in which the cancer has advanced to infiltrate into the muscularis mucosa 105, an additional high frequency component is generated.

The disease state score calculation section 97 calculates a disease state score indicating the disease state of the observation target based on the distribution pattern calculated by the distribution pattern generation section 96. Specifically, the distribution pattern calculated by the distribution pattern generation section 96 is compared with a reference pattern stored in advance in the reference pattern storage section 98, and the similarity is calculated as a disease state score. In the present embodiment, the distribution pattern generation section 96 calculates the distribution of oxygen saturation as a distribution pattern. Therefore, corresponding to this, a template of the distribution of oxygen saturation generated based on the past clinical data or the like is stored in advance as a reference pattern in the reference pattern storage section 98. The disease state score calculation section 97 calculates a disease state score (similarity) by performing a matching between the distribution pattern obtained from the distribution pattern generation section 96 and the reference pattern.

Figure 15:
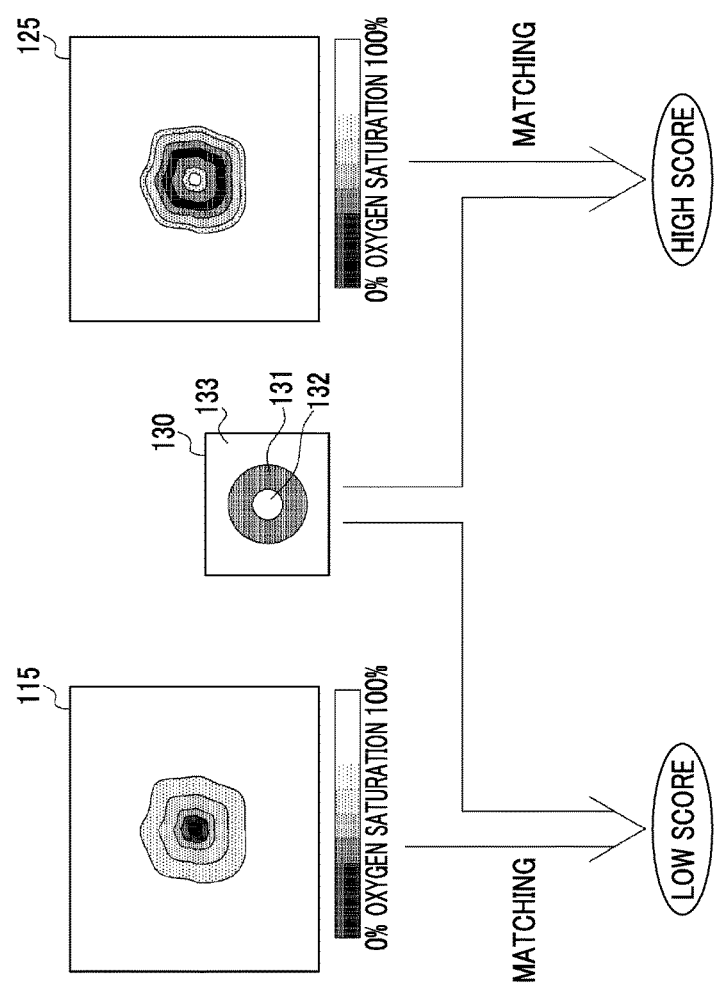
FIG. 15 is an explanatory diagram showing the relationship between a reference pattern and a disease state score.

As shown in FIG. 15, a reference pattern 130 is, for example, a specific oxygen saturation distribution shape having a high oxygen region 132, in which the oxygen saturation is equal to or greater than a predetermined value, in a low oxygen region 131 in which the oxygen saturation is less than the predetermined value. That is, the reference pattern 130 is an oxygen saturation distribution shape obtained by simulating the distribution of the oxygen saturation of advanced cancer. In addition, the predetermined value of the oxygen saturation for distinguishing the low oxygen region 131 and the high oxygen region 132 is set based on clinical data. The oxygen saturation of a peripheral portion 133 of the low oxygen region 131 is a value obtained by simulating the oxygen saturation of the normal tissue.

The disease state score calculation section 97 enlarges or reduces the reference pattern 130, and matches the enlarged or reduced reference pattern 130 with the distribution pattern calculated by the distribution pattern generation section 96. The distribution pattern 125 (refer to FIG. 14) of advanced cancer having a high oxygen region in a low oxygen region has a higher similarity with the reference pattern 130 than the distribution pattern 115 (refer to FIG. 13) of early cancer that does not have a high oxygen region in a low oxygen region. Therefore, the disease state score is large in case of observing advanced cancer. In a case in which there is no cancer, a low oxygen region is not included in the distribution pattern calculated by the distribution pattern generation section 96. Therefore, the disease state score in this case is smaller than that in the case of observing early cancer.

As described above, the disease state score is a high score in a case in which a high oxygen region is present in a low oxygen region. However, it is preferable that the disease state score increases as the proportion of the high oxygen region in the low oxygen region increases. Since the proportion of the high oxygen region in the low oxygen region corresponds to the range of infiltration into the muscularis mucosa 105, the degree of progression of advanced cancer can be evaluated in more detail and objectively by setting the disease state score in this manner. In order to calculate a disease state score that increases according to the proportion of the high oxygen region in the low oxygen region, for example, it is preferable to prepare a plurality of reference patterns in advance by changing the area of the high oxygen region 132, perform a matching between the reference patterns and a distribution pattern, and determine the sum of lesion scores obtained by matching with the respective reference patterns as a final lesion score. In addition, reference patterns having different proportions of the high oxygen region in the low oxygen region may be used by being generated from the reference pattern 130 by calculation. In addition, a value obtained by correcting the similarity obtained by matching according to the proportion of the high oxygen region in the low oxygen region may be used as a lesion score.

The disease state score calculated by the disease state score calculation section 97 is input to the image display signal generation unit 66, and is displayed on the monitor 18 together with the oxygen saturation image.

Figure 16:
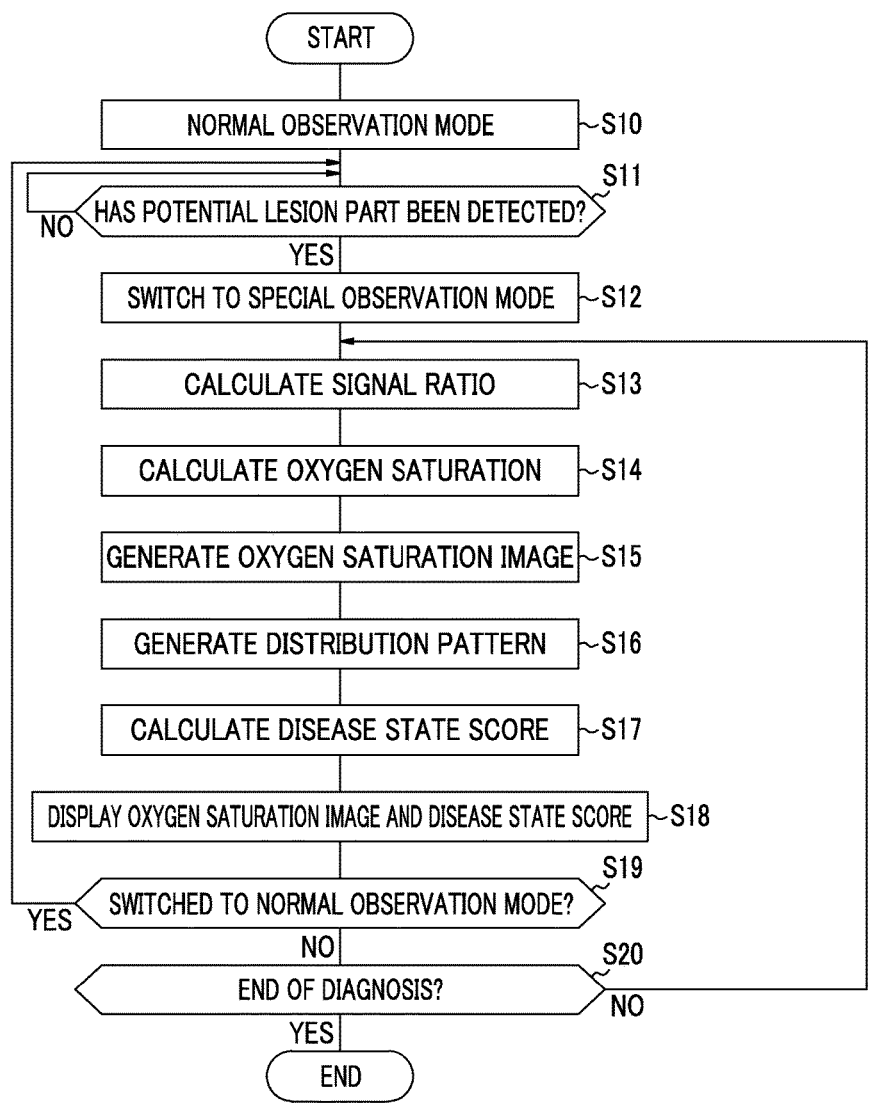
FIG. 16 is a flowchart showing the operation of the endoscope system.

Next, the flow of observation using the endoscope system 10 of the present embodiment will be described with reference to the flowchart in FIG. 16. First, in the normal observation mode, screening is performed from the most distant view state (S10). In the normal observation mode, a normal observation image is displayed on the monitor 18. In a case in which a part that is likely to be a lesion (hereinafter, referred to as a potential lesion part), such as a brownish area or rubor, is found in this screening (S11), the mode selector SW 22b is operated for switching to the special observation mode (S12). Then, in the special observation mode, the potential lesion part is examined.

In the special observation mode, the first and second white light beams are alternately emitted to irradiate the observation target in synchronization with the imaging frame of the sensor 48. Accordingly, the sensor 48 outputs the R1 image signal, the G1 image signal, and the B1 image signal in a frame in which the first white light is emitted, and outputs the R2 image signal, the G2 image signal, and the B2 image signal in a frame in which the second white light is emitted. Based on the image signals of the two frames, the signal ratio calculation section 81 calculates the signal ratio B1/G2 and the signal ratio R2/G2 for each pixel (S13). Then, based on the signal ratio B1/G2 and the signal ratio R2/G2, the oxygen saturation calculation section 83 calculates the oxygen saturation for each pixel (S14). After the calculation of the oxygen saturation, the image generation section 87 generates an oxygen saturation image by multiplying each of the B2 image signal, the G2 image signal, and the R2 image signal by a gain corresponding to the oxygen saturation (S15).

The distribution pattern generation section 96 calculates a distribution pattern showing the distribution regarding the oxygen saturation based on the data of oxygen saturation calculated by the oxygen saturation calculation section 83 (S16), and the disease state score calculation section 97 calculates a disease state score based on the distribution pattern (S17).

Figure 17:
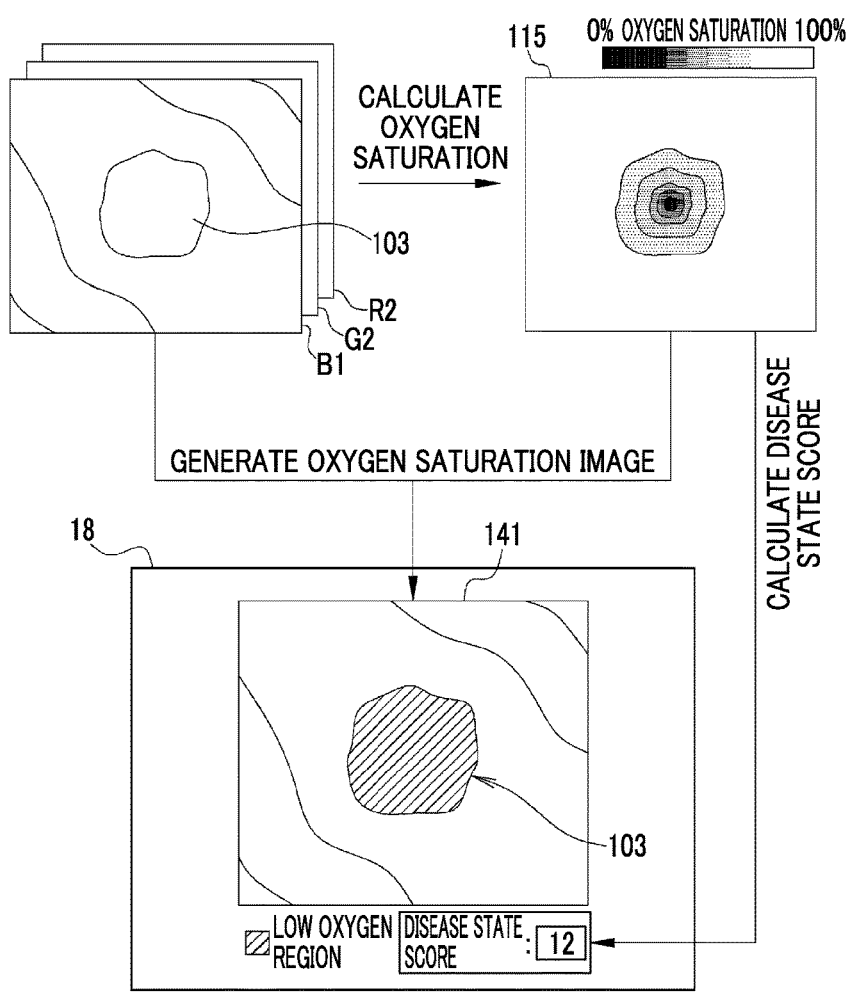
FIG. 17 is an explanatory diagram showing a display example in a case in which there is early cancer.
Figure 18:
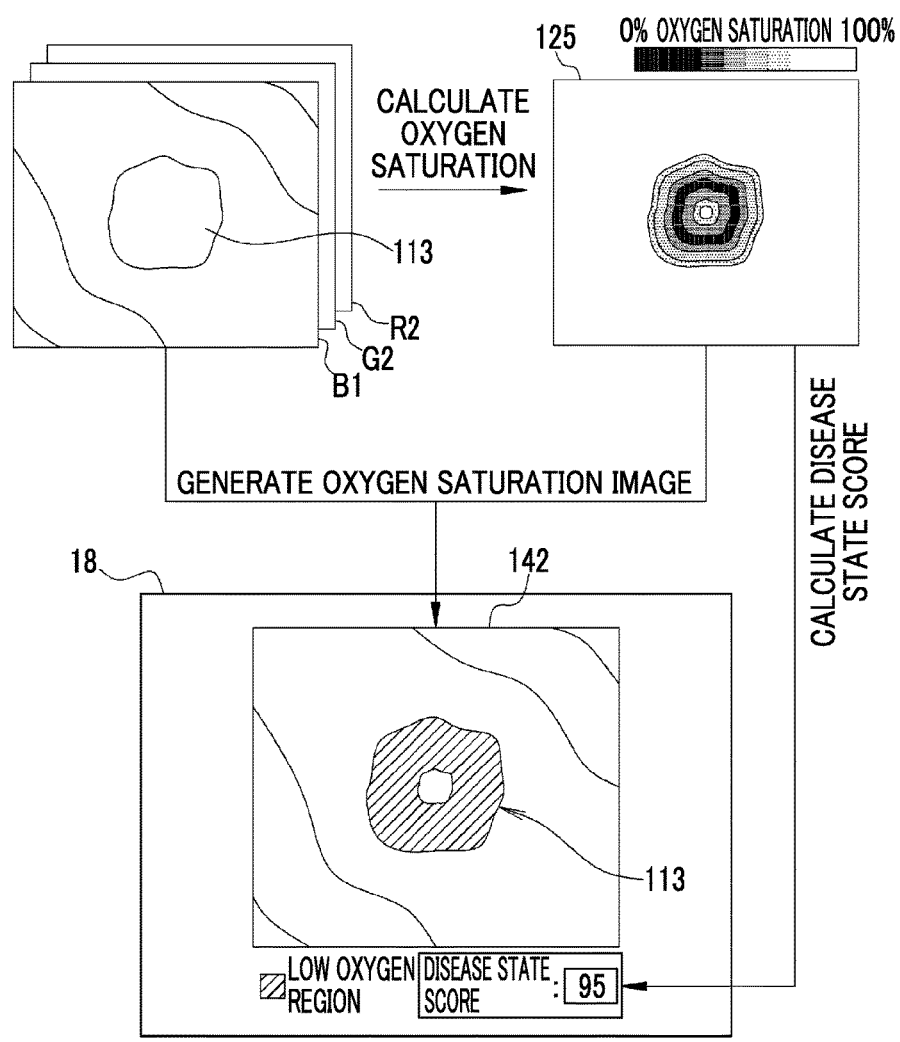
FIG. 18 is an explanatory diagram showing a display example in a case in which there is advanced cancer.

The oxygen saturation image and the disease state score that have been generated and calculated as described above are displayed on the monitor 18 (S18). For example, as shown in FIG. 17, in a case in which the lesion tissue is early cancer, an oxygen saturation image 141 obtained by pseudo-coloring almost the entire cancer tissue 103 and the disease state score "12" are displayed on the monitor 18. In addition, as shown in FIG. 18, in a case in which the lesion tissue is advanced cancer, an oxygen saturation image 142, in which the cancer tissue 113 having a high oxygen region of normal color is projected in a pseudo-colored low oxygen region, and the disease state score "95" are displayed on the monitor 18.

As described above, the entire cancer tissue 103 is pseudo-colored by early cancer, and the cancer tissue 113 is pseudo-colored in an annular shape by advanced cancer. Therefore, the doctor can determine whether the lesion tissue is early cancer or advanced cancer (or whether or not the tissue is cancer) by observing the oxygen saturation image displayed on the monitor 18. In addition, in the endoscope system 10, since a lesion score obtained by objectively evaluating the possibility of infiltration is displayed on the monitor 18, it is possible to check the possibility of infiltration more easily by viewing the lesion score. Therefore, it is possible to perform detailed diagnosis including the degree of progression of cancer accurately and easily.

The display of such oxygen saturation (oxygen saturation image) is continuously performed until switching to the normal observation mode occurs (S19). In case of finishing the diagnosis, the insertion unit 21 of the endoscope 12 is extracted from the subject (S20).

As described above, the endoscope system 10 can assist the diagnosis of a doctor not only by displaying the oxygen saturation image on the monitor 18 but also by calculating the lesion score and displaying the lesion score on the monitor 18. The endoscope system 10 can provide assistance based on the calculation and display of the lesion score in real time in the course of observing the observation target. In particular, the endoscope system 10 can score the degree of progression of a lesion into the observation target (in the depth direction of the lesion) by observing the surface of the observation target. Therefore, it is possible to present information for assisting the diagnosis more quickly (for example, without reducing the frame rate of observation) than in a case of observing the observation target for each depth by changing the wavelength used for observation or the like.

Figure 19:
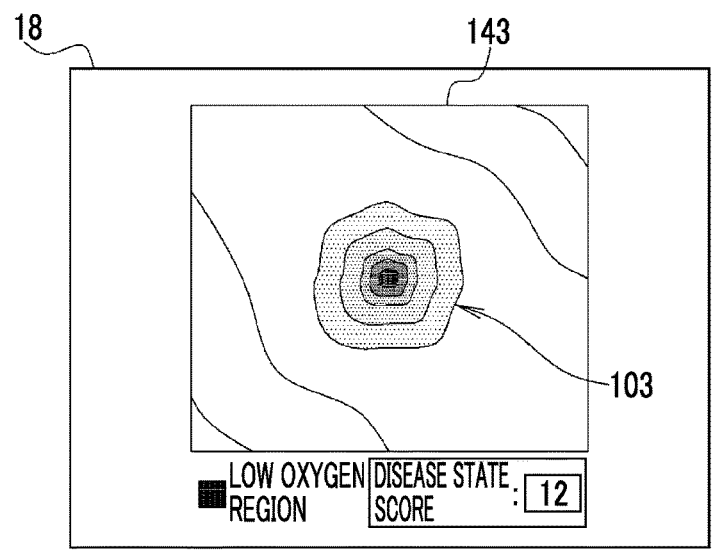
FIG. 19 is an explanatory diagram showing another display example in a case in which there is early cancer.
Figure 20:
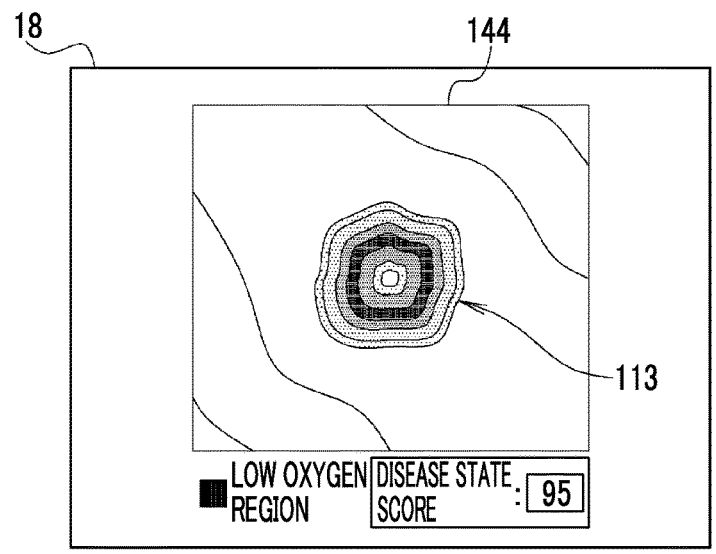
FIG. 20 is an explanatory diagram showing another display example in a case in which there is advanced cancer.

In addition, although the endoscope system 10 generates an oxygen saturation image by pseudo-coloring the low oxygen region with the oxygen saturation of 60% as a boundary and displays the oxygen saturation image, the oxygen saturation may be divided more finely in a stepwise manner, and pseudo-coloring may be performed so as to generate different colors in respective steps. For example, by changing a gain by which each image signal is multiplied according to the oxygen saturation, different colors can be displayed in the respective steps of the oxygen saturation. In this case, as shown in FIGS. 19 and 20, it is possible to display oxygen saturation images 143 and 144 in which the distribution shape of the oxygen saturation of the cancer tissue 103 of early cancer or the cancer tissue 113 of advanced cancer appears in detail.

In addition, although the endoscope system 10 calculates and displays a disease state score to provide assistance in determining the degree of progression of cancer, it is also possible to calculate and display a disease state score to provide assistance in determining the degree of progression of lesions (inflammation, ulceration, and the like) other than cancer using the same method.

In addition, although the disease state score that increases according to the degree of progression of cancer is calculated and displayed in the endoscope system 10, a disease state score that decreases according to the degree of progression may be calculated conversely. For example, the disease state score calculation section 97 may calculate the reciprocal of the similarity between the distribution pattern obtained from the distribution pattern generation section 96 and the reference pattern as a disease state score. In this case, the disease state score is the largest in a case in which there is no high oxygen region in the low oxygen region, and the disease state score is reduced in a case in which a high oxygen region is present in the low oxygen region. As the proportion of the high oxygen region in the low oxygen region increases, the disease state score is further reduced. Accordingly, the smallness of the disease state score indicates the degree of progression of cancer.

Figure 21:
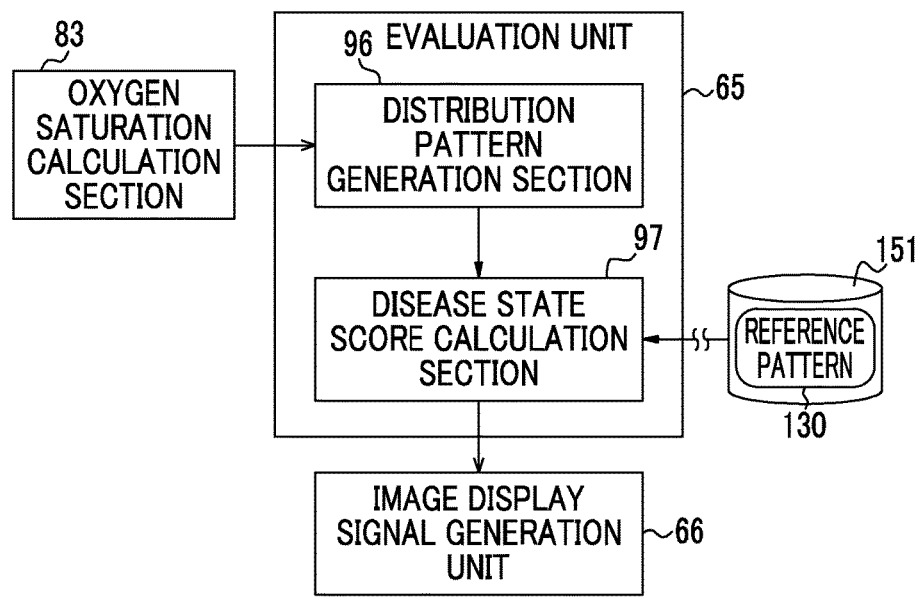
FIG. 21 is a block diagram showing an evaluation unit in case of acquiring a reference pattern from the outside.

In the endoscope system 10, the reference pattern storage section 98 that stores the reference pattern 130 in advance is provided in the evaluation unit 65. Accordingly, as shown in FIG. 21, the reference pattern 130 may be acquired from an external database 151 that is connected to the processor device 16 through a network. Thus, when the reference pattern 130 is acquired from the external database 151, even if the reference pattern 130 is updated based on the latest case, it is possible to calculate a lesion score using the optimal reference pattern always even without maintenance to update the data of the reference pattern storage section 98.

Figure 22:
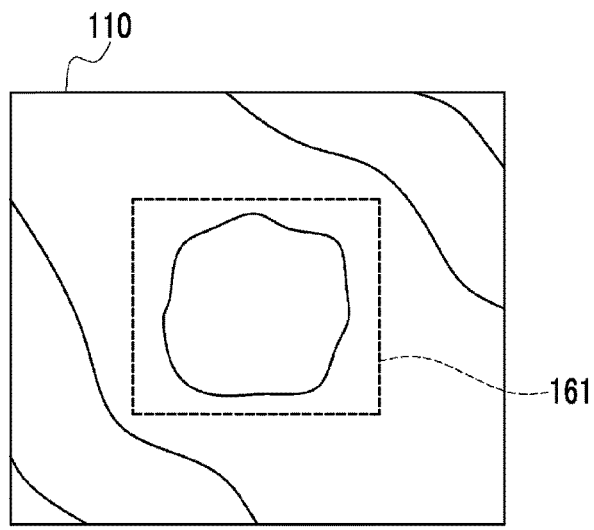
FIG. 22 is an explanatory diagram showing a region of interest.

In the endoscope system 10, a region for calculating the distribution pattern and the lesion score in the distribution pattern generation section 96 and the disease state score calculation section 97 is not specified. However, the distribution pattern generation section 96 and the disease state score calculation section 97 may calculate a distribution pattern and a lesion score for a region of interest 161 specified in advance as shown in FIG. 22. In this manner, it is possible to quickly calculate the lesion score. For example, the region of interest 161 is a region that a doctor specifies while observing the normal observation image 110 (may be an oxygen saturation image). Specifying the region of interest 161 can be performed by the processor device 16. Needless to say, a distribution pattern and a lesion score may be calculated for the entire observation range in a case in which the region of interest 161 is not specified, and a distribution pattern and a lesion score may be calculated for the specified region of interest 161 in a case in which the region of interest 161 is specified.

In addition, the region of interest 161 may be automatically specified by the endoscope system 10. For example, a region-of-interest extraction section that extracts a region, which includes a low oxygen region and has a predetermined size and a predetermined shape (for example, a rectangular shape), as a region of interest from the distribution patterns 115 and 125 generated by the distribution pattern generation section 96 may be provided in the evaluation unit 65, and a disease state score may be calculated for the extracted region of interest.

In the endoscope system 10, the distribution pattern generation section 96 calculates one distribution pattern (distribution shape of the oxygen saturation), and the disease state score calculation section 97 calculates a lesion score corresponding to the distribution pattern. However, in case of generating a plurality of distribution patterns including other distribution patterns, such as a distribution pattern of the inclination of oxygen saturation, a result of calculation using a lesion score calculated for each distribution pattern, such as a sum value of lesion scores calculated for the respective distribution patterns or a value obtained by adding a weighting to the lesion score calculated for each distribution pattern, as a lesion score that is finally calculated and displayed.

[Second Embodiment]

Figure 23:
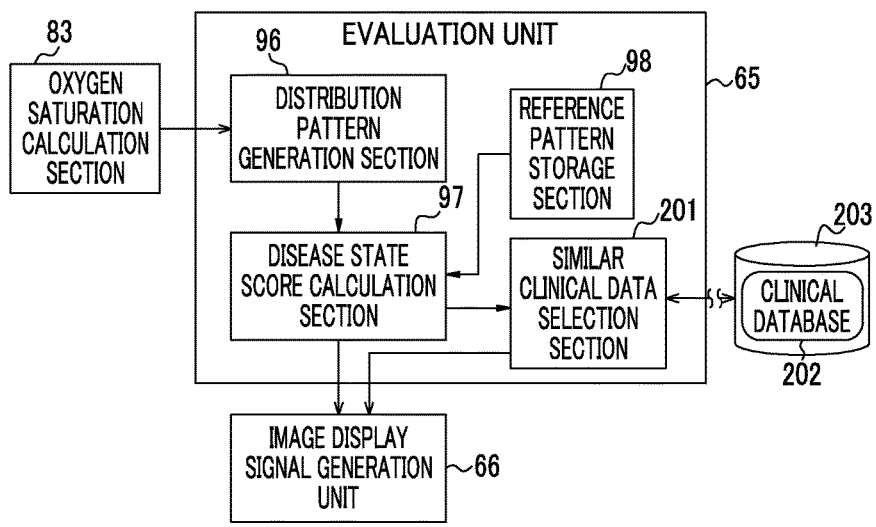
FIG. 23 is a block diagram showing an evaluation unit of a second embodiment.

As shown in FIG. 23, in an endoscope system of a second embodiment, a similar clinical data selection section 201 is further provided in the evaluation unit 65. Other configurations are the same as the endoscope system 10 of the first embodiment.

Figure 24:
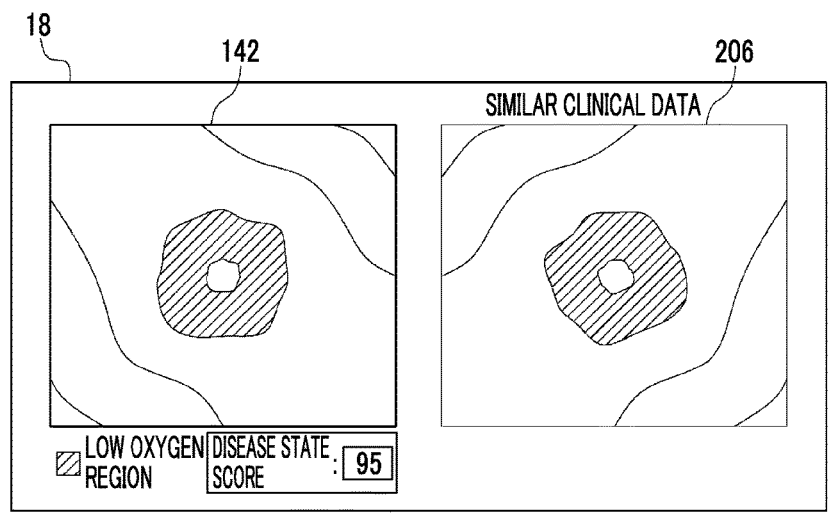
FIG. 24 is an explanatory diagram showing a display example of the second embodiment.

The similar clinical data selection section 201 acquires a disease state score from the disease state score calculation section 97, and selects a past case having a disease state score, which is close to (or matches) the acquired disease state score, from a clinical database 202 stored in a plurality of pieces of clinical data 203. Then, the selected clinical data (hereinafter, referred to as similar clinical data) is input to the image display signal generation unit 66. As a result, as shown in FIG. 24, for example, an oxygen saturation image 206 included in the similar clinical data is displayed on the monitor 18 side by side with an oxygen saturation image 142 of the observation target.

In the endoscope system of the second embodiment, it is possible to present not only the disease state score but also the oxygen saturation image 206 of similar clinical data to a doctor in real time.

Other than the oxygen saturation image 206, other kinds of images, such as a normal observation image included in the similar clinical data or a narrowband light image in the case of observation using narrowband light, may be displayed on the monitor 18. In addition, in a case in which not only various kinds of images but also the recording of a diagnostic result, such as a disease name, or performed treatment or the effect is included in the similar clinical data, these may be displayed on the monitor 18. Such various kinds of recording of similar cases assist the diagnosis of a doctor.

The clinical database 202 may be an external database that is connected to the endoscope system through a network, or may be a database provided in the endoscope system (processor device 16). In a case in which there is a plurality of disease state scores that are the same scores, the latest one of the plurality of disease state scores may be selected and displayed, or a disease state score that has been referred to the most may be selected and displayed. The clinical data displayed as similar clinical data may be set in advance for each disease state score. In addition, the similar clinical data may be narrowed down and selected depending on the similarity with the observation target, such as the age, sex, or observation part of the subject, other than the disease state score.

In the endoscope system of the second embodiment, a piece of similar clinical data is selected. However, a plurality of pieces of similar clinical data may be selected and displayed on the monitor 18. In a case in which a plurality of pieces of similar clinical data are selected, a list of the plurality of pieces of similar clinical data may be displayed on the monitor 18, and the oxygen saturation image of the similar clinical data selected from the list by the doctor may be displayed on the monitor 18.

[Third Embodiment]

Figure 25:
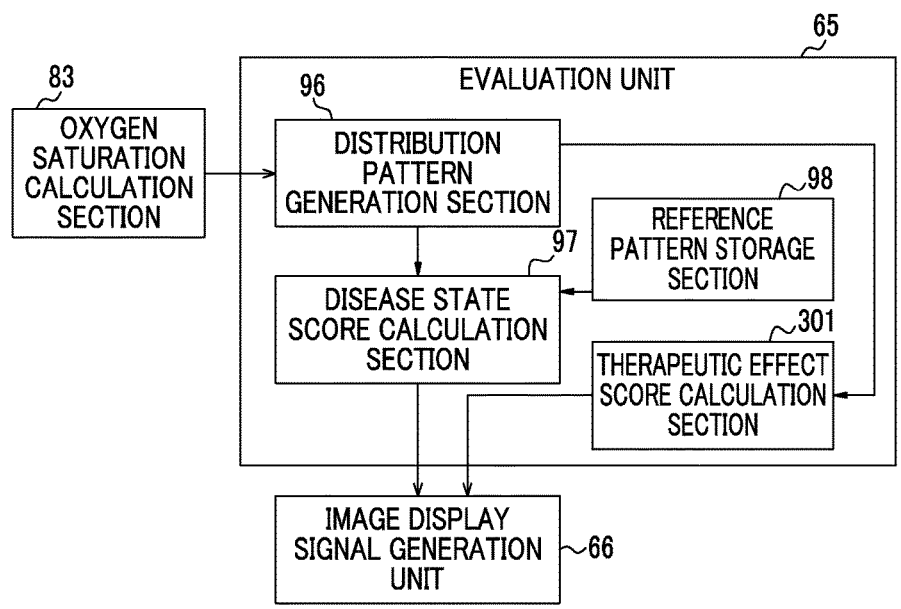
FIG. 25 is a block diagram showing an evaluation unit of a third embodiment.

As shown in FIG. 25, in an endoscope system of a third embodiment, a therapeutic effect score calculation section 301 is provided in the evaluation unit 65 in the endoscope system 10 of the first embodiment, and other configurations are the same as the endoscope system 10 of the first embodiment.

Figure 26:
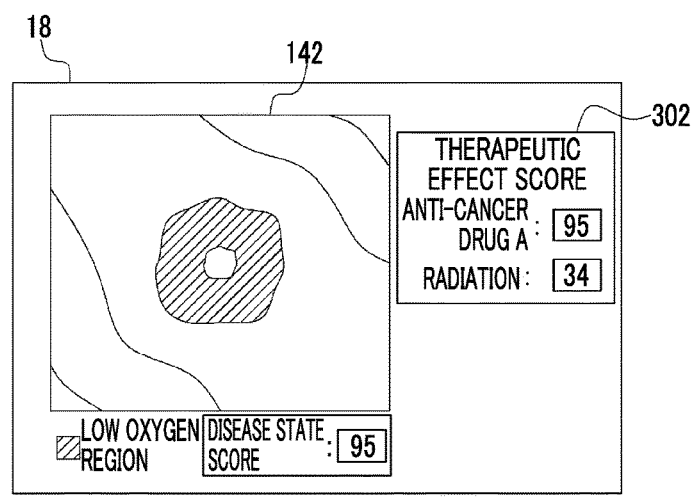
FIG. 26 is an explanatory diagram showing a display example of the third embodiment.

The therapeutic effect score calculation section 301 acquires a distribution pattern from the distribution pattern generation section 96, and calculates a therapeutic effect score showing the therapeutic effect using a specific treatment method based on the acquired distribution pattern. Specifically, a therapeutic effect score is calculated based on the distribution pattern (distribution shape of oxygen saturation) or information calculated from the distribution pattern (area of a low oxygen region, proportion of a high oxygen region in a low oxygen region, or the like). The therapeutic effect score calculation section 301 displays a therapeutic effect score 302 on the monitor 18 side by side with the oxygen saturation image 142 of the observation target, as shown in FIG. 26, by inputting the calculated therapeutic effect score to the image display signal generation unit 66. In a case in which the lesion is cancer, examples of the specific treatment method and the therapeutic effect include anti-cancer drugs and the efficacy, radiation therapy and the efficacy, and surgery and the prognosis (a survival rate, a recurrence possibility, or a metastatic possibility).

For example, in the case of anti-cancer drugs, the effect of anti-cancer drugs in the low oxygen region is low since the blood flow is poor, and the effect of anti-cancer drugs in the high oxygen region is high. Therefore, the therapeutic effect score calculation section 301 sets the therapeutic effect score of anti-cancer drugs to be low in a case in which a number of low oxygen regions are present, and sets the therapeutic effect score of anti-cancer drugs to be high in a case in which a number of high oxygen regions are present (in a case in which the proportion of the high oxygen region in the low oxygen region is large). In the case of radiation therapy, since the amount of generation of free radicals is reduced in the low oxygen region, the therapeutic effect is low. Accordingly, the therapeutic effect score calculation section 301 sets the therapeutic effect score of radiation therapy to be low in a case in which a number of low oxygen regions are present, and sets the therapeutic effect score of radiation therapy to be high in a case in which a number of high oxygen regions are present (in a case in which the proportion of the high oxygen region in the low oxygen region is large).

[Fourth Embodiment]

Figure 27:
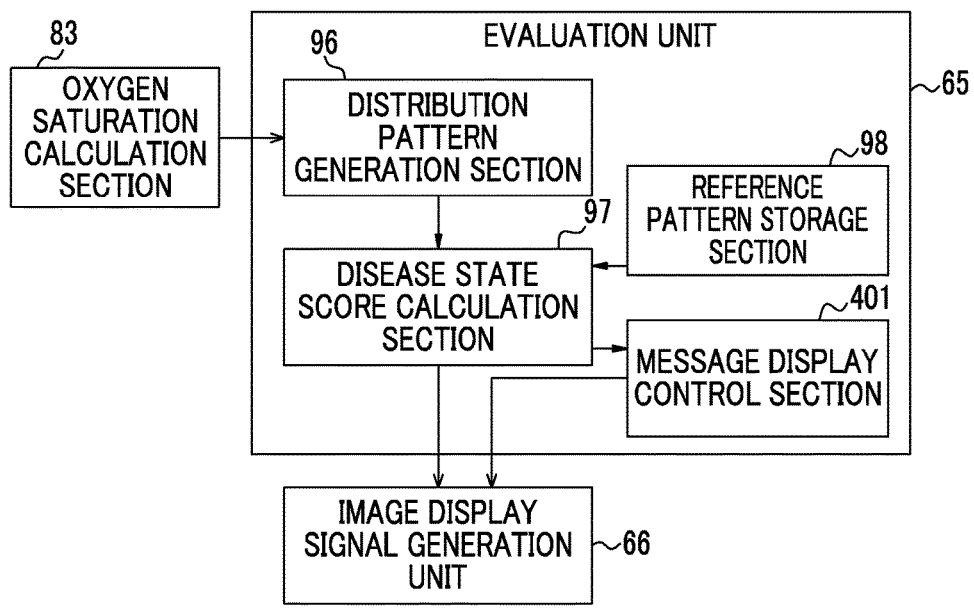
FIG. 27 is a block diagram showing an evaluation unit of a fourth embodiment.

As shown in FIG. 27, in an endoscope system of a fourth embodiment, a message display control section 401 is added to the evaluation unit 65 in the endoscope system 10 of the first embodiment, and other configurations are the same as the endoscope system 10 of the first embodiment.

Figure 28:
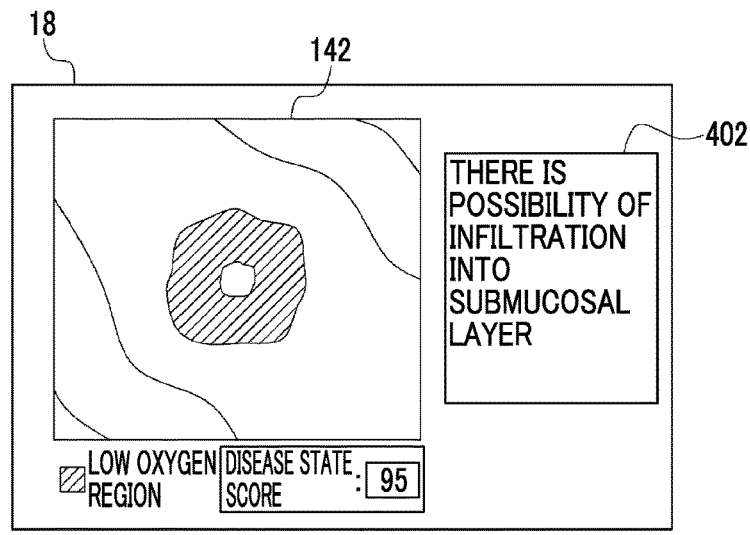
FIG. 28 is an explanatory diagram showing a display example of the fourth embodiment.

The message display control section 401 acquires a disease state score from the disease state score calculation section 97, and monitors the value of the acquired disease state score. In addition, for example, the message display control section 401 inputs information corresponding to the disease state scores, such as a warning, to the image display signal generation unit 66. Therefore, as shown in FIG. 28, a message 402 corresponding to the disease state score is displayed on the monitor 18 side by side with the oxygen saturation image 142 of the observation target. For example, in a case in which the disease state score is high, a possibility of infiltration into the muscularis mucosa 105 or the submucosal tissue layer 106 is high. Accordingly, in a case in which the disease state score is equal to or greater than a specific value set in advance, it is preferable to display the message 402 to give a warning about the possibility of infiltration. Although the message display control section 401 always monitors the disease state score, the message 402 may not be displayed. The message may be displayed only in the case of a specific disease state, for example, in a case in which the disease state score is equal to or greater (smaller) than a specific value or in a case in which the disease state score is in a predetermined range.

[Fifth Embodiment]

Figure 29:
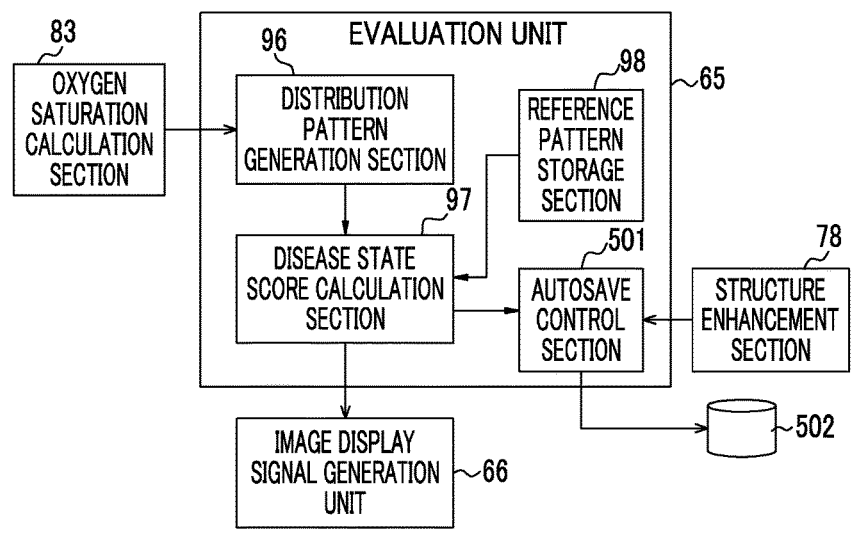
FIG. 29 is a block diagram showing an evaluation unit of a fifth embodiment.

As shown in FIG. 29, in an endoscope system of a fifth embodiment, an autosave control section 501 is added to the evaluation unit 65 in the endoscope system 10 of the first embodiment, and other configurations are the same as the endoscope system 10 of the first embodiment.

The autosave control section 501 acquires the disease state score from the disease state score calculation section 97, and monitors the value. In a case in which the disease state score is a value equal to or greater than a predetermined specified value, for example, the oxygen saturation image output from the structure enhancement section 78 is acquired, and is automatically stored in a storage unit 502. Automatic saving of an oxygen saturation image that is performed by the autosave control section 501 is performed even if a doctor who operates the endoscope system does not perform an operation for saving a still image. In the oxygen saturation image to be automatically saved, a disease state score is associated therewith to be stored together. For example, the disease state score is recorded on the header of the oxygen saturation image as supplementary information.

In a case in which the disease state score is a high score, the possibility of advanced cancer is high, and a possibility that the oxygen saturation image will be stored as a still image by the doctor is typically high. However, even if the doctor has forgotten to store the oxygen saturation image as a still image, the oxygen saturation image is automatically stored by the autosave control section 501. Accordingly, since it is not necessary to repeat the inspection, the burden on the doctor and the subject is reduced.

In addition, in a case in which the disease state score is a high score, it is not necessary to automatically store oxygen saturation images of all the frames. For example, autosaving by the autosave control section 501 may be performed at predetermined frame intervals.

The similar clinical data selection section 201 of the second embodiment, the therapeutic effect score calculation section 301 of the third embodiment, the message display control section 401 of the fourth embodiment, and the autosave control section 501 of the fifth embodiment can be used in combination with each other.

[Sixth Embodiment]

Figure 30:
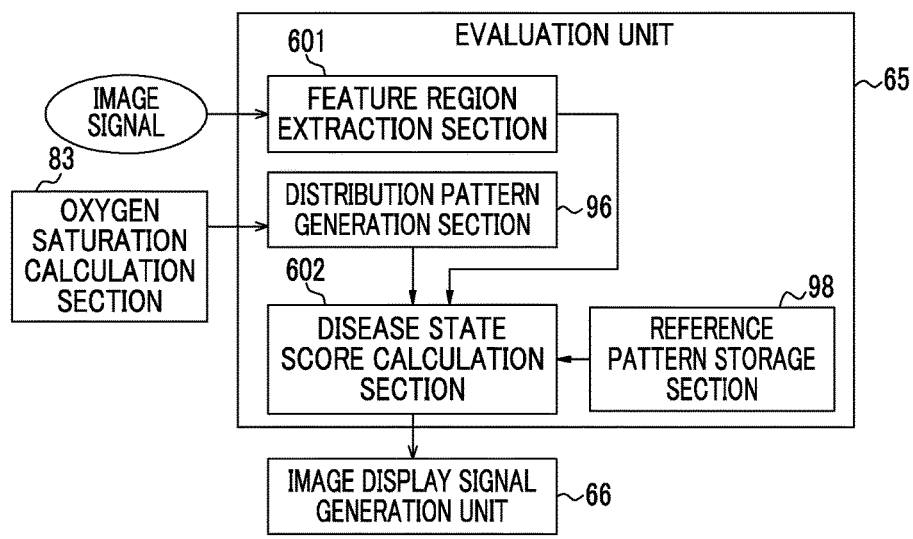
FIG. 30 is a block diagram showing an evaluation unit of a sixth embodiment.

As shown in FIG. 30, an endoscope system of a sixth embodiment includes a feature region extraction section 601 in the evaluation unit 65. In addition, a disease state score calculation section 602 calculates a disease state score based on the distribution pattern of the oxygen saturation in a feature region extracted by the feature region extraction section 601. Other configurations are the same as that of the endoscope system 10 of the first embodiment.

Figure 31:
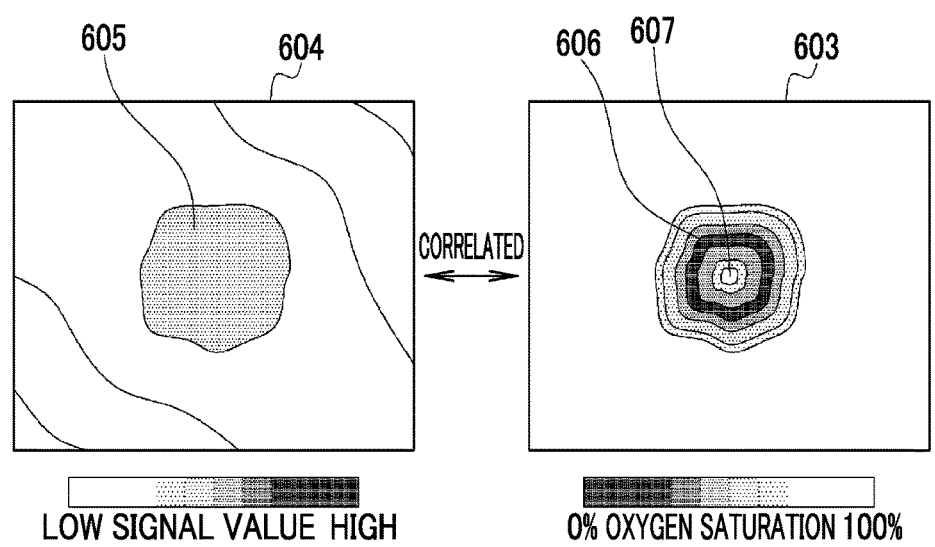
FIG. 31 is an explanatory diagram showing a method of calculating a distribution pattern in the sixth embodiment.

The feature region extraction section 601 acquires an image signal, and extracts a portion suspected to be a lesion as a feature region of the observation target. For example, as shown in FIG. 31, the feature region extraction section 601 extracts a region where rubor is strong (hereinafter, referred to as a rubor region) 605 as a feature region based on the acquired image signal.

The disease state score calculation section 602 calculates a disease state score indicating the disease state of the observation target based on the distribution pattern of the oxygen saturation in the rubor region 605 extracted by the feature region extraction section 601. For example, as a distribution pattern 603 of the oxygen saturation, if a distribution pattern in which a high oxygen region 607 is present in a low oxygen region 606 overlaps the rubor region 605, a possibility that the rubor region 605 is due to the construction of new blood vessels by cancer tissue is high. Therefore, by calculating the disease state score based on the distribution pattern of the oxygen saturation in the rubor region 605, the presence of cancer tissue and the degree of progression can be expressed particularly accurately as a disease state score.

In the present embodiment, the disease state score calculation section 602 sets a disease state score in a case in which a high oxygen region having an oxygen saturation equal to or greater than a predetermined value is present in the rubor region 605 to be greater than a disease state score in a case in which there is no high oxygen region in the rubor region 605. In a case in which a high oxygen region is present in the rubor region 605, the disease state score is made to increase as the proportion of a high oxygen region with respect to the rubor region 605 increases. In this manner, the degree of progression of cancer can be expressed more clearly by the disease state score. Needless to say, the disease state score calculation section 602 may set a disease state score in a case in which a high oxygen region having an oxygen saturation equal to or greater than a predetermined value is present in the rubor region 605 to be smaller than a disease state score in a case in which there is no high oxygen region in the rubor region 605. In this case, in a case in which a high oxygen region is present in the rubor region 605, the disease state score is made to decrease as the proportion of a high oxygen region with respect to the rubor region 605 increases. Also in this case, the degree of progression of cancer can be expressed more clearly by the disease state score.

In addition, the feature region extraction section 601 can extract the rubor region 605 using a B2 image signal or a G2 image signal. This is because the absorption by blood hemoglobin in a wavelength band near, for example, 420 nm or 550 nm is large (refer to FIG. 10) and accordingly the contrast due to absorption of hemoglobin appears largely in the B2 image signal or the G2 image signal including the information of the wavelength band and the presence of blood vessels can be easily determined. Needless to say, a B1 image signal or a G2 image signal may be used. In addition, based on a plurality of image signals including the R1 (R2) image signal, the rubor region 605 may be extracted.

Although the rubor region 605 is extracted as a feature region, an uplifted region of the observation target may also be extracted as a feature region.

As in the first embodiment, the disease state score is input to the image display signal generation unit 66 and is displayed on the monitor 18. Therefore, the second to fifth embodiments can be used in combination with the sixth embodiment.

[Seventh Embodiment]

Figure 32:
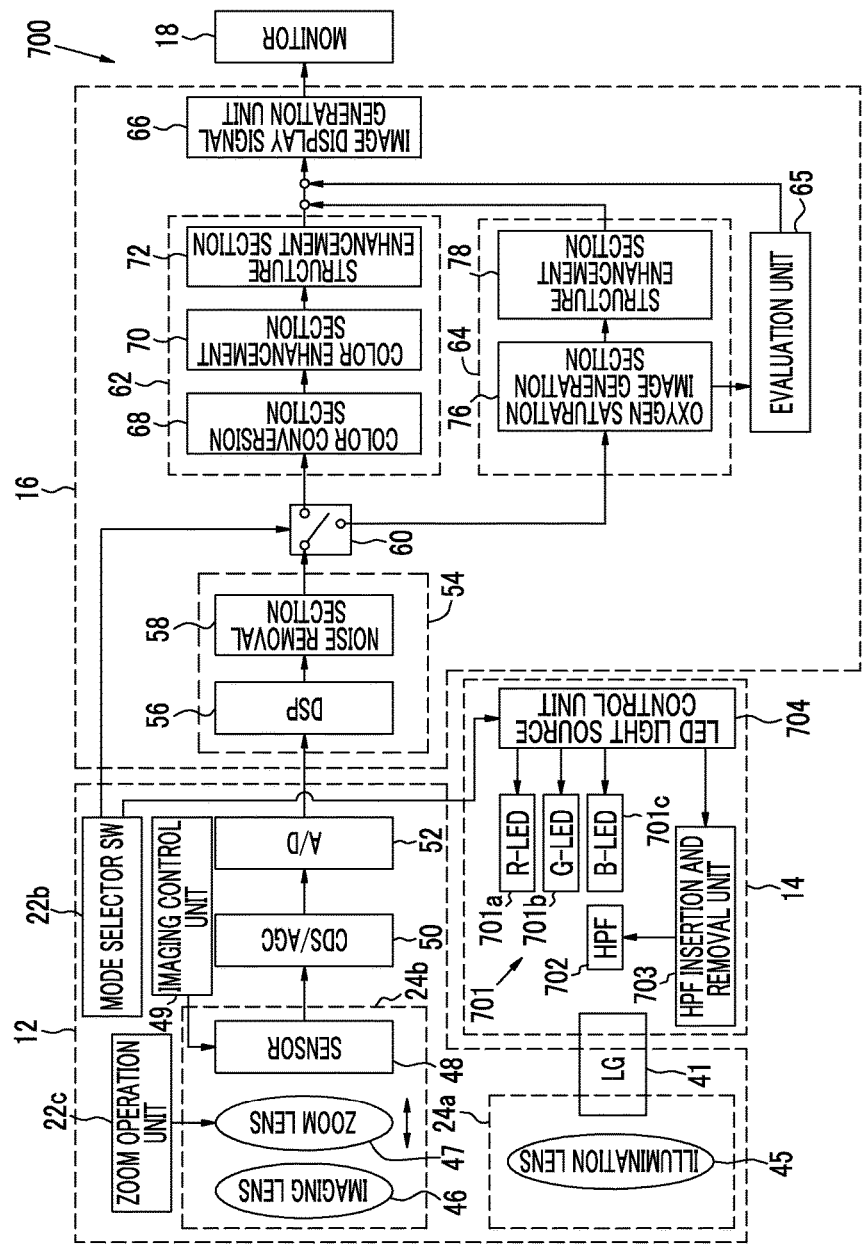
FIG. 32 is a block diagram of an endoscope system of a seventh embodiment.

As shown in FIG. 32, in a light source device 14 of an endoscope system 700, a light emitting diode (LED) light source unit 701 and an LED light source control unit 704 are provided instead of the first and second blue laser light sources 34 and 36 and the light source control unit 40. In addition, the phosphor 44 is not provided in an illumination optical system 24a of the endoscope system 700. Other than these, the endoscope system 700 is the same as the endoscope system 10 of the first embodiment.

Figure 33:
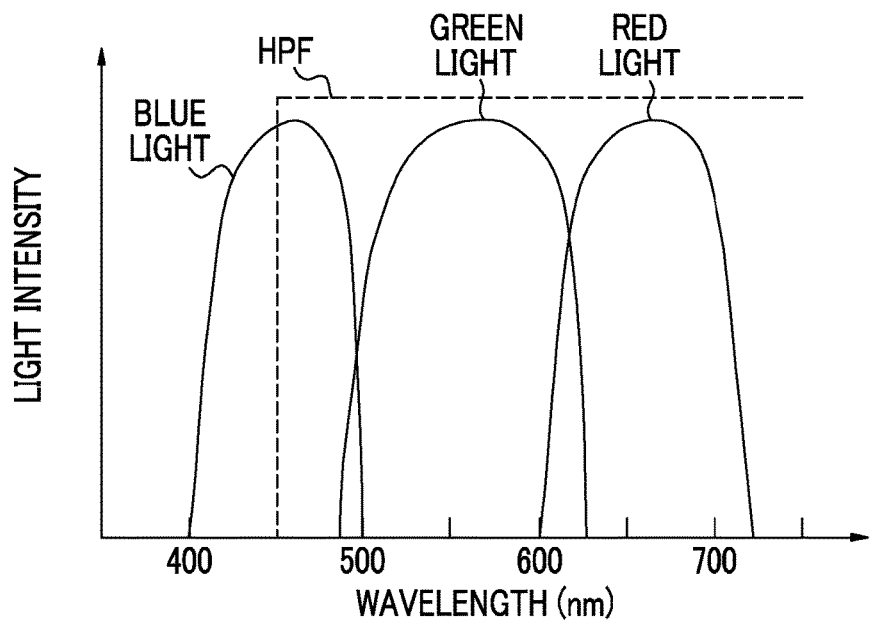
FIG. 33 is a graph showing the light emission band of an LED and the characteristics of an HPF.

The LED light source unit 701 includes an R-LED 701a, a G-LED 701b, and a B-LED 701c as light sources that emit light limited to a specific wavelength band. As shown in FIG. 33, the R-LED 701a emits red band light (hereinafter, simply referred to as red light) in a red region of 600 nm to 720 nm, and the G-LED 701b emits green band light (hereinafter, simply referred to as green light) in a green region of 480 nm to 620 nm. The B-LED 701c emits blue band light (hereinafter, simply referred to as blue light) in a blue region of 400 nm to 500 nm.

The LED light source unit 701 includes a high pass filter (HPF) 702 that is removably inserted on the optical path of the blue light emitted from the B-LED 701c. The high pass filter 702 cuts blue light in a wavelength band of 450 nm or less, and allows light in a wavelength band higher than 450 nm to be transmitted therethrough.

The cutoff wavelength (450 nm) of the high pass filter 702 is a wavelength at which the absorption coefficient of oxygenated hemoglobin and the absorption coefficient of reduced hemoglobin are almost equal (refer to FIG. 10), and the absorption coefficient of oxygenated hemoglobin and the absorption coefficient of reduced hemoglobin are reversed in the order of magnitude with the cutoff wavelength as a boundary. In the present embodiment, the correlation stored in the correlation storage section 82 is that the absorption coefficient of oxygenated hemoglobin is greater than the absorption coefficient of reduced hemoglobin. Accordingly, in a signal based on the wavelength band equal to or lower than the cutoff wavelength, the signal ratio B1/G2 is lower than the original value measured at 473 nm. This is a cause of calculating incorrect oxygen saturation. For this reason, when acquiring the B1 image signal for calculating the oxygen saturation, the high pass filter 702 blocks light in a wavelength band equal to or lower than the cutoff wavelength from being emitted to the observation target.

Accordingly, the high pass filter 702 is inserted before the B-LED 701c in the special observation mode, and is retracted to the retraction position in the normal observation mode. The insertion and removal of the high pass filter 702 are performed by an HPF insertion and removal unit 703 under the control of the LED light source control unit 704.

Figure 34:
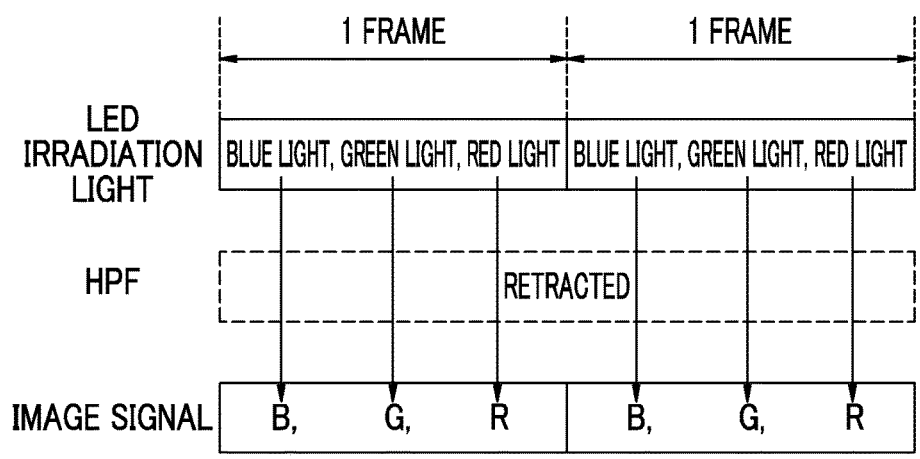
FIG. 34 is an explanatory diagram showing imaging control in the normal observation mode in the seventh embodiment.

The LED light source control unit 704 controls ON/OFF of the LEDs 701a to 701c of the LED light source unit 701 and the insertion and removal of the high pass filter 702. Specifically, as shown in FIG. 34, in the normal observation mode, the LED light source control unit 704 turns on all of the LEDs 701a to 701c and removes the high pass filter 702 from the optical path of the B-LED 701c.

Figure 35:
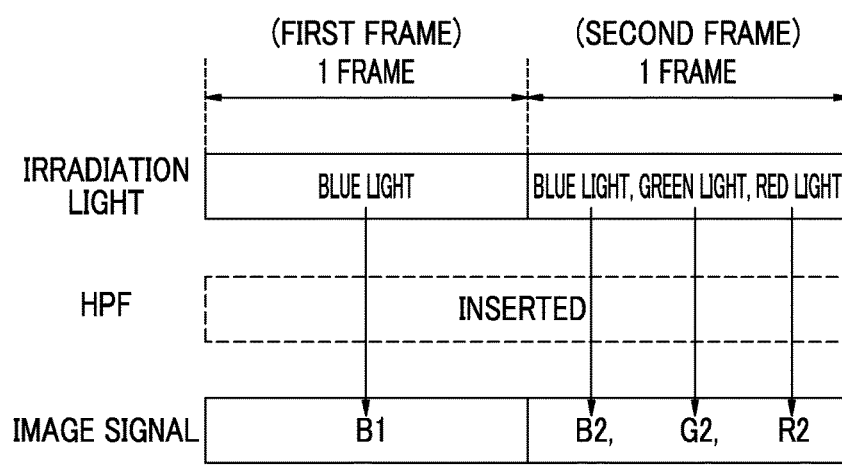
FIG. 35 is an explanatory diagram showing imaging control in the special observation mode in the seventh embodiment.

On the other hand, as shown in FIG. 35, in the special observation mode, the LED light source control unit 704 inserts the high pass filter 702 on the optical path of the B-LED 701c. Then, in the first frame, the B-LED 701c is turned on and the R-LED 701a and the G-LED 701b are turned off, so that blue light in which a wavelength band equal to or lower than 450 nm has been cut is emitted to the observation target. Then, in the second frame, all of the R-LED 701a, the G-LED 701b, and the B-LED 701c are turned on, so that white light configured to include blue light obtained by cutting a wavelength band equal to or lower than 450 nm from the blue light emitted from the B-LED 701c, red light emitted from the R-LED 701a, and green light emitted from the G-LED 701b is emitted to the observation target. In this manner, the sensor 48 outputs the B1 image signal in the first frame, and outputs the R2 image signal, the G2 image signal, and the B2 image signal in the second frame. Accordingly, subsequent processing can be performed in the same manner as in the endoscope system 10 of the first embodiment.

In the seventh embodiment, in both the first and second frames in the special observation mode, the observation target is imaged in a state in which the high pass filter 702 is inserted. However, the high pass filter 702 may be inserted only in the first frame, and the high pass filter 702 may be removed in the second frame. In addition, in the first frame in the special observation mode, only the B-LED 701c is turned on to emit only the blue light to the observation target. However, also in the first frame, the R-LED 701a and the G-LED 701b may be turned on to output the R1 image signal and the G1 image signal to the sensor 48.

[Eighth Embodiment]

Figure 36:
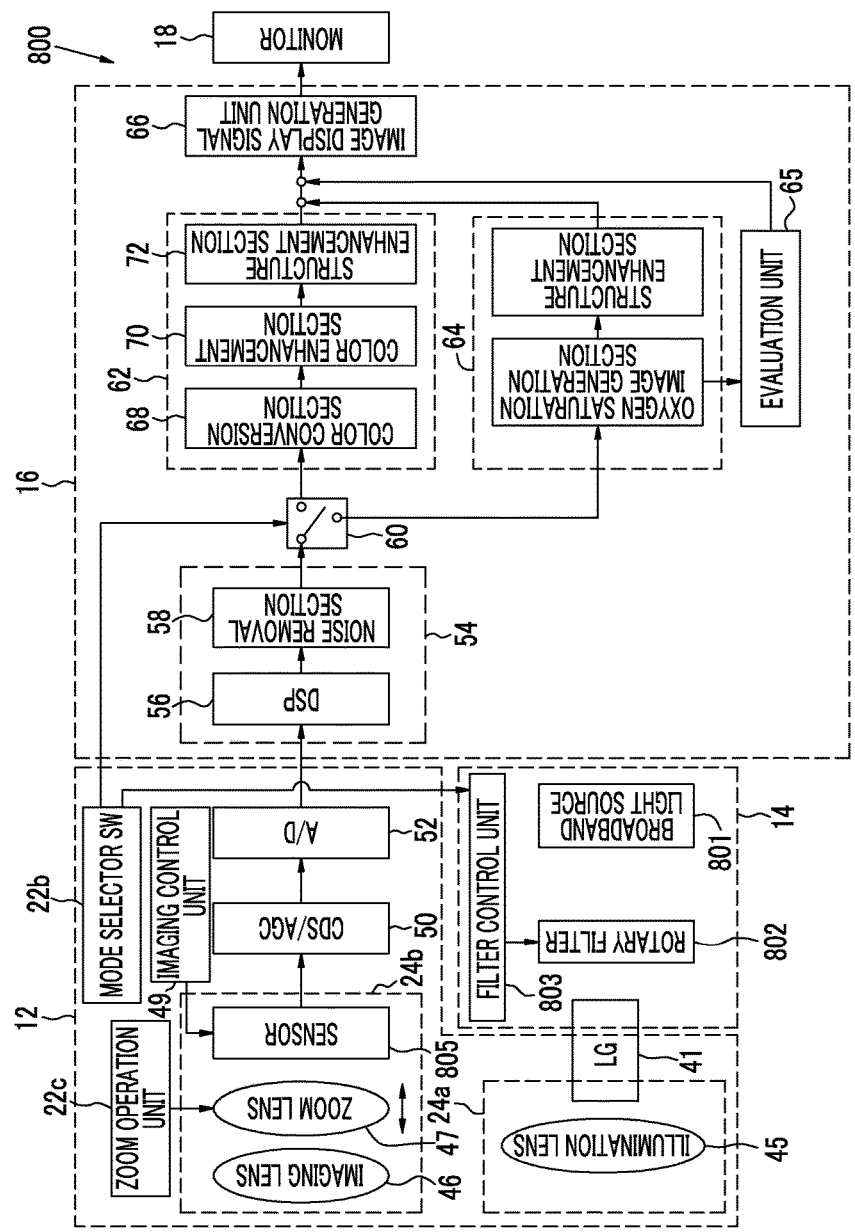
FIG. 36 is a block diagram of an endoscope system according to an eighth embodiment.

As shown in FIG. 36, in a light source device 14 of an endoscope system 800, a broadband light source 801, a rotary filter 802, and a rotary filter control unit 803 are provided instead of the first and second blue laser light sources 34 and 36 and the light source control unit 40. A sensor 805 of the endoscope system 800 is a monochrome imaging device in which no color filter is provided. Other than these, the endoscope system 800 is the same as the endoscope system 10 of the first embodiment.

The broadband light source 801 is, for example, a xenon lamp or a white LED, and emits white light having a wavelength in a wavelength band ranging from blue to red. The rotary filter 802 includes a normal observation mode filter 810 and a special observation mode filter 811 (refer to FIG. 37), and can move in a radial direction between a first position for normal observation mode to place a normal observation mode filter 810 on the optical path, in which the white light emitted from the broadband light source 801 is incident on the light guide 41, and a second position for special observation mode to place a special observation mode filter 811 on the optical path. The movement of the rotary filter 802 to the first and second positions is controlled by the rotary filter control unit 803 according to the selected observation mode. In addition, the rotary filter 802 rotates according to the imaging frame of the sensor 805 in a state of being placed at the first or second position. The rotation speed of the rotary filter 802 is controlled by the rotary filter control unit 803 according to the selected observation mode.

Figure 37:
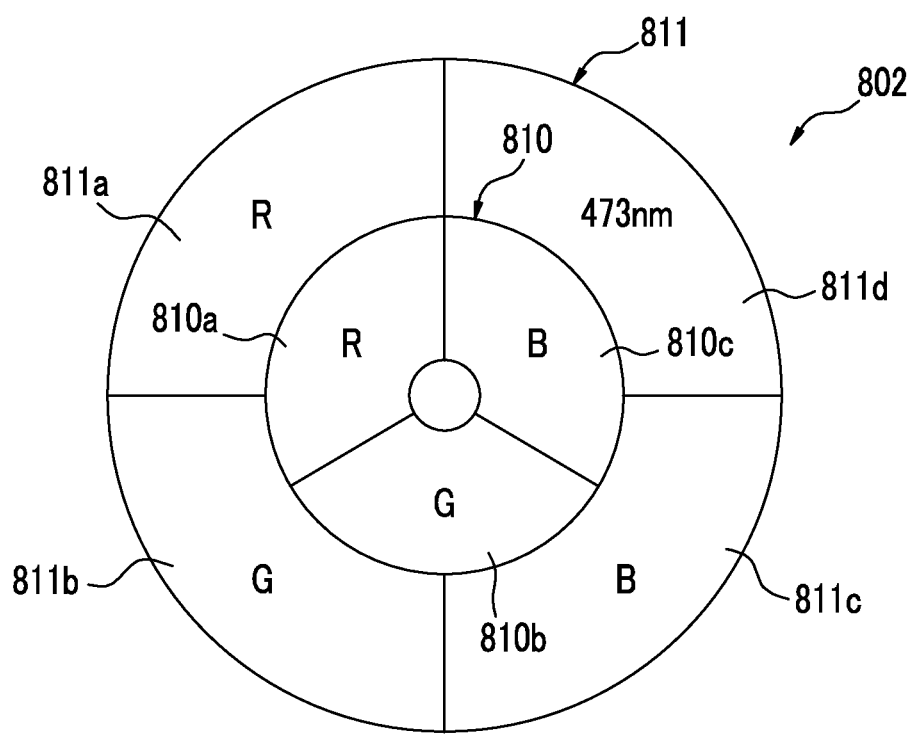
FIG. 37 is a plan view of a rotary filter.

As shown in FIG. 37, the normal observation mode filter 810 is provided in the inner peripheral portion of the rotary filter 802. The normal observation mode filter 810 includes an R filter 810a that transmits red light, a G filter 810b that transmits green light, and a B filter 810c that transmits blue light. Therefore, when the rotary filter 802 is placed at the first position for normal light observation mode, white light from the broadband light source 801 is incident on one of the R filter 810a, the G filter 810b, and the B filter 810c according to the rotation of the rotary filter 802. As a result, red light, green light, and blue light are sequentially emitted to the observation target according to the transmitted filter, and the sensor 805 outputs sequentially an R image signal, a G image signal, and a B image signal by imaging the observation target with reflected light of the red light, the green light, and the blue light.

The special observation mode filter 811 is provided in the outer peripheral portion of the rotary filter 802. The special observation mode filter 811 includes an R filter 811a that transmits red light, a G filter 811b that transmits green light, a B filter 811c that transmits blue light, and a narrowband filter 811d that transmits narrowband light of 473±10 nm. Therefore, when the rotary filter 802 is placed at the second position for normal light observation mode, white light from the broadband light source 801 is incident on one of the R filter 811a, the G filter 811b, the B filter 811c, and the narrowband filter 811d according to the rotation of the rotary filter 802. As a result, red light, green light, blue light, and narrowband light (473 nm) are sequentially emitted to the observation target according to the transmitted filter, and the sensor 805 outputs sequentially an R image signal, a G image signal, a B image signal, and a narrowband image signal by imaging the observation target with reflected light of the red light, the green light, the blue light, and the narrowband light.

The R image signal and the G image signal obtained in the special observation mode correspond to the R1 (or R2) image signal and the G1 (or G2) image signal in the first embodiment, respectively. In addition, the B image signal obtained in the special observation mode corresponds to the B2 image signal in the first embodiment, and the narrowband image signal corresponds to the B1 image signal. Accordingly, subsequent processing can be performed in the same manner as in the endoscope system 10 of the first embodiment.

Although the oxygen saturation is calculated based on the signal ratio B1/G2 and the signal ratio R2/G2 in the first to eighth embodiments, it is also possible to calculate the oxygen saturation based on only the signal ratio B1/G2. In this case, it is preferable to store the correlation between the signal ratio B1/G2 and the oxygen saturation in the correlation storage section 82.

Although the oxygen saturation image obtained by imaging the oxygen saturation is generated and displayed in the first to eighth embodiments, a blood volume image obtained by imaging the blood volume may be generated and displayed in addition to the generation and display of the oxygen saturation image. Since the blood volume is correlated with the signal ratio R2/G2, a blood volume image obtained by imaging the blood volume can be generated by assigning different colors according to the signal ratio R2/G2.

In the first to eighth embodiments, the oxygen saturation is calculated. However, instead of or in addition to the oxygen saturation, other kinds of biological function information, such as an oxygenated hemoglobin index that is calculated from "blood volume (signal ratio R2/G2)×oxygen saturation (%)" or a reduced hemoglobin index that is calculated from "blood volume×(1−oxygen saturation) (%)", may be calculated.

EXPLANATION OF REFERENCES 10, 700, 800: endoscope system
18: monitor
65: evaluation unit
76: oxygen saturation image generation section
83: oxygen saturation calculation section
96: distribution pattern generation section
97, 602: disease state score calculation section
115, 125: distribution pattern
130: reference pattern
161: region of interest (designated region)
201: similar clinical data selection section
301: therapeutic effect score calculation section
401: message display control section
501: autosave control section
601: feature region extraction section

What is claimed is:

1. An endoscope system, comprising:
a light source device that includes a plurality of light sources emitting light having different center wavelengths and a light source control unit respectively controlling the light, to irradiate an observation target;
an image sensor that images the observation target with reflected light of the light and outputs an image signal;
a processor configured to:
calculate an oxygen saturation of the observation target with corrected influence of dependency on blood volume based on the image signal corresponding to the light;
acquire data of the oxygen saturation calculated for each pixel, and generate a distribution pattern showing a distribution of the oxygen saturation;
compare the distribution pattern with a reference pattern that is a specific distribution shape, and calculate a similarity between the reference pattern and the distribution pattern as a disease state score indicating a disease state of the observation target based on the distribution pattern; and
a monitor that displays the disease state score or information of lesion based on the disease state score.

2. The endoscope system according to claim 1, wherein the disease state score in a case in which a high oxygen region having the oxygen saturation equal to or greater than a predetermined value is present in a low oxygen region having the oxygen saturation less than the predetermined value is greater than the disease state score in a case in which the high oxygen region is not present in the low oxygen region.

3. The endoscope system according to claim 2, wherein, in a case in which the high oxygen region is present in the low oxygen region, the disease state score increases as a proportion of the high oxygen region with respect to the low oxygen region increases.

4. The endoscope system according to claim 1, wherein the disease state score in a case in which a high oxygen region having the oxygen saturation equal to or greater than a predetermined value is present in a low oxygen region having the oxygen saturation less than the predetermined value is smaller than the disease state score in a case in which the high oxygen region is not present in the low oxygen region.

5. The endoscope system according to claim 4, wherein, in a case in which the high oxygen region is present in the low oxygen region, the disease state score decreases as a proportion of the high oxygen region with respect to the low oxygen region increases.

6. The endoscope system according to claim 1, wherein the reference pattern that is a specific distribution shape is a pattern in which a high oxygen region having the oxygen saturation equal to or greater than a predetermined value is present in a low oxygen region having the oxygen saturation less than the predetermined value.

7. The endoscope system according to claim 1, wherein the processor is configured to generate the distribution pattern for a region of interest designated in advance, and calculate the disease state score for the region of interest.

8. The endoscope system according to claim 1, wherein the processor is configured to compare the distribution pattern with clinical data referring to a database in which a plurality of pieces of the past clinical data are stored in advance, selects similar clinical data which is similar to the distribution pattern among the pieces of clinical data, and displays the similar clinical data on the monitor.

9. The endoscope system according to claim 8, wherein the processor is configured to display an oxygen saturation image included in the similar clinical data on the monitor.

10. The endoscope system according to claim 1, wherein the processor is configured to calculate a therapeutic effect score, which indicates a therapeutic effect of a specific treatment method, based on the distribution pattern, and displays the therapeutic effect score on the monitor.

11. The endoscope system according to claim 1, wherein the processor is configured to, in a case in which the disease state score is a value equal to or greater than a specified value, associating the disease state score with an oxygen saturation image generated based on the image signal and the oxygen saturation and automatically store them.

12. The endoscope system according to claim 1, wherein the monitor displays the disease state score or information of lesion based on the disease state score in a case in which the disease state score is equal to or greater than a specific value.

13. The endoscope system according to claim 1, wherein the processor is configured to extract a feature region of the observation target based on the image signal, and
wherein the processor is configured to calculate the disease state score based on the distribution pattern of the feature region.

14. The endoscope system according to claim 13, wherein the processor is configured to extract the feature region based on a blue image signal obtained from a blue pixel of the image sensor or a green image signal obtained from a green pixel of the image sensor.

15. The endoscope system according to claim 13, wherein the feature region is a rubor region, and
the disease state score in a case in which a high oxygen region having the oxygen saturation equal to or greater than a predetermined value is present in the rubor region is greater than the disease state score in a case in which the high oxygen region is not present in the rubor region.

16. The endoscope system according to claim 14, wherein the feature region is a rubor region, and
the disease state score in a case in which a high oxygen region having the oxygen saturation equal to or greater than a predetermined value is present in the rubor region is greater than the disease state score in a case in which the high oxygen region is not present in the rubor region.

17. The endoscope system according to claim 15, wherein, in a case in which the high oxygen region is present in the rubor region, the disease state score increases as a proportion of the high oxygen region with respect to the rubor region increases.

18. The endoscope system according to claim 16, wherein, in a case in which the high oxygen region is present in the rubor region, the disease state score increases as a proportion of the high oxygen region with respect to the rubor region increases.

19. The endoscope system according to claim 13, wherein the feature region is a rubor region, and
the disease state score in a case in which a high oxygen region having the oxygen saturation equal to or greater than a predetermined value is present in the rubor region is smaller than the disease state score in a case in which the high oxygen region is not present in the rubor region.

20. The endoscope system according to claim 14, wherein the feature region is a rubor region, and
the disease state score in a case in which a high oxygen region having the oxygen saturation equal to or greater than a predetermined value is present in the rubor region is smaller than the disease state score in a case in which the high oxygen region is not present in the rubor region.

21. The endoscope system according to claim 19, wherein, in a case in which the high oxygen region is present in the rubor region, the disease state score decreases as a proportion of the high oxygen region with respect to the rubor region increases.

22. The endoscope system according to claim 20, wherein, in a case in which the high oxygen region is present in the rubor region, the disease state score decreases as a proportion of the high oxygen region with respect to the rubor region increases.

23. The endoscope system according to claim 1, wherein the processor is configured to monitor the disease state score and displays a message corresponding to the disease state score on the monitor.

24. A processor device for an endoscope system including a light source device that includes a plurality of light sources emitting light having different center wavelengths and a light source control unit respectively controlling the light, to irradiate an observation target, an image sensor for imaging the observation target with reflected light of the light and outputting an image signal, and a monitor, the processor device configured to:
calculate an oxygen saturation of the observation target with corrected influence of dependency on blood volume based on the image signal corresponding to the light;
acquire data of the oxygen saturation calculated for each pixel, and generate a distribution pattern showing a distribution of the oxygen saturation; and
compare the distribution pattern with a reference pattern that is a specific distribution shape, and calculate a similarity between the reference pattern and the distribution pattern as a disease state score indicating a disease state of the observation target based on the distribution pattern.

25. The processor device for an endoscope system according to claim 24, the processor device further configured to:
extract a feature region of the observation target based on the image signal,
wherein the processor is configured to calculate the disease state score based on the distribution pattern of the feature region.

26. An operation method for an endoscope system for operating the endoscope system according to claim 1 including a light source device that includes a plurality of light sources emitting light having different center wavelengths and a light source control unit respectively controlling the light, to irradiate an observation target, an image sensor for imaging the observation target with reflected light of the light and outputting an image signal, and a monitor, the operation method comprising:
a step of calculating an oxygen saturation of the observation target with corrected influence of dependency on blood volume based on the image signal corresponding to the light;
a step of acquiring data of the oxygen saturation calculated for each pixel, and generating a distribution pattern showing a distribution of the oxygen saturation;
a step of comparing the distribution pattern with a reference pattern that is a specific distribution shape, and calculating a similarity between the reference pattern and the distribution pattern as a disease state score indicating a disease state of the observation target based on the distribution pattern; and
a step of displaying the disease state score or information of lesion based on the disease state score.

27. The operation method for an endoscope system according to claim 26, further comprising:
a step of extracting a feature region of the observation target based on the image signal,
wherein, in the step of calculating the disease state score, the disease state score is calculated based on the distribution pattern of the feature region.

28. An operation method for the processor device according to claim 24 for processing an image signal obtained by imaging an observation target, the operation method comprising:
a step of calculating an oxygen saturation of the observation target based on the image signal;
a step of generating a distribution pattern showing a distribution of the oxygen saturation; and
a step of calculating a disease state score indicating a disease state of the observation target based on the distribution pattern.

29. The operation method for a processor device according to claim 28, further comprising:
a step of extracting a feature region of the observation target based on the image signal,
wherein, in the step of calculating the disease state score, the disease state score calculation unit calculates the disease state score based on the distribution pattern of the feature region.

* * * * *